(12) United States Patent
Park et al.

(10) Patent No.: US 12,019,820 B2
(45) Date of Patent: Jun. 25, 2024

(54) WEARABLE ELECTRONIC DEVICE COMPRISING ANTENNA AND ELECTRODE

(71) Applicant: SAMSUNG ELECTRONICS CO., LTD., Suwon-si (KR)

(72) Inventors: Jaehyuck Park, Suwon-si (KR); Jeongmin Park, Suwon-si (KR); Namseok Chang, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 17/991,784

(22) Filed: Nov. 21, 2022

(65) Prior Publication Data

US 2023/0168761 A1 Jun. 1, 2023

Related U.S. Application Data

(63) Continuation of application No. PCT/KR2022/018085, filed on Nov. 16, 2022.

(30) Foreign Application Priority Data

Nov. 29, 2021 (KR) .................. 10-2021-0167395
Dec. 29, 2021 (KR) .................. 10-2021-0190563

(51) Int. Cl.
  *G06F 3/041* (2006.01)
  *G06F 3/01* (2006.01)
  *H01Q 1/27* (2006.01)

(52) U.S. Cl.
  CPC .......... *G06F 3/0416* (2013.01); *G06F 3/015* (2013.01); *G06F 3/016* (2013.01); *H01Q 1/273* (2013.01)

(58) Field of Classification Search
  CPC ..... G06F 1/1652; G06F 1/1677; G06F 1/1616
  See application file for complete search history.

(56) References Cited

U.S. PATENT DOCUMENTS 8,332,019 B2   12/2012  Shimuta et al.
10,031,483 B2* 7/2018   Seo ................. A44C 5/147
(Continued)

FOREIGN PATENT DOCUMENTS

JP  2017-188914   10/2017
JP  2018-201694   12/2018
(Continued)

OTHER PUBLICATIONS

KR20210046211 Sep. 28, 2021 Watch-Type Electronic Device Including Antenna. Kim Jeonghwan; (Year: 2019).*
(Continued)

*Primary Examiner* — Van N Chow
(74) *Attorney, Agent, or Firm* — NIXON & VANDERHYE P.C.

(57) ABSTRACT

Disclosed is a wearable electronic device including: a housing including a first surface forming a front surface of the wearable electronic device, a second surface facing away from the first surface, and a side surface surrounding an internal space between the first surface and the second surface, a first electrode area positioned in a part of the first surface and the side surface and including a plurality of electrodes, an antenna positioned in a part of the first surface and the side surface and defined by the first electrode area and a segment area, a display visible through at least part of the first surface, a second electrode area positioned on the second surface, a processor, and a memory operatively connected to the processor and including instructions. When a touch input to at least part of the first electrode area is detected, the wearable electronic device obtains a biometric signal through the first electrode area, the second electrode area, or a combination of the first electrode area and the second electrode area and performs wireless communication through the antenna.

17 Claims, 19 Drawing Sheets

(56) References Cited

U.S. PATENT DOCUMENTS

| | | | |
|---|---|---|---|
| 10,223,905 | B2 | 3/2019 | Zdeblick et al. |
| 10,433,759 | B2 | 10/2019 | Ahn et al. |
| 10,610,157 | B2 | 4/2020 | Pandya et al. |
| 10,720,044 | B2 | 7/2020 | Zdeblick et al. |
| 10,987,054 | B2 | 4/2021 | Pandya et al. |
| 11,016,535 | B1 | 5/2021 | Tsai et al. |
| 11,294,428 | B2 | 4/2022 | Tsai et al. |
| 11,432,766 | B2 | 9/2022 | Pandya et al. |
| 11,482,773 | B2 * | 10/2022 | Wei .................. H01Q 1/48 |
| 11,526,195 | B2 | 12/2022 | Tsai et al. |
| 11,666,276 | B2 | 6/2023 | Lee et al. |
| 11,793,444 | B2 * | 10/2023 | Vajdic .................. G16H 40/67 |
| 2016/0198977 | A1 | 7/2016 | Eom et al. |
| 2016/0324440 | A1 | 11/2016 | Kim et al. |
| 2021/0030359 | A1 | 2/2021 | Jeong et al. |
| 2021/0169420 | A1 | 6/2021 | Jung |
| 2023/0010168 | A1 | 1/2023 | Jung et al. |
| 2023/0233153 | A1 * | 7/2023 | Kwon .................. A61B 5/681 |
| | | | 600/301 |

FOREIGN PATENT DOCUMENTS

| | | |
|---|---|---|
| KR | 10-1270089 | 5/2013 |
| KR | 10-2015-0081735 | 7/2015 |
| KR | 10-2016-0086715 | 7/2016 |
| KR | 10-2017-0114615 | 10/2017 |
| KR | 10-2018-0078164 A | 7/2018 |
| KR | 10-2020-0027010 | 3/2020 |
| KR | 10-2106416 | 5/2020 |
| KR | 10-2021-0015005 | 2/2021 |
| KR | 10-2021-0046211 | 4/2021 |
| KR | 10-2021-0046211 A | 4/2021 |
| KR | 10-2021-0073274 | 6/2021 |
| KR | 10-2021-0081998 A | 7/2021 |
| KR | 10-2021-0103730 A | 8/2021 |
| KR | 10-2021-0116944 | 9/2021 |

OTHER PUBLICATIONS

Search Report and Written Opinion dated Mar. 8, 2023 issued in International Patent Application No. PCT/KR2022/018085.

* cited by examiner

WEARABLE ELECTRONIC DEVICE COMPRISING ANTENNA AND ELECTRODE

CROSS-REFERENCE TO RELATED APPLICATIONS

This application is a continuation of International Application No. PCT/KR2022/018085 designating the United States, filed on Nov. 16, 2022, in the Korean Intellectual Property Receiving Office and claiming priority to Korean Patent Application No. 10-2021-0167395, filed on Nov. 29, 2021, in the Korean Intellectual Property Office, and to Korean Patent Application No. 10-2021-0190563, filed on Dec. 29, 2021, in the Korean Intellectual Property Office, the disclosures of all of which are incorporated by reference herein their entireties.

BACKGROUND

1. Field

The disclosure relates to an electronic device including an antenna and an electrode.

2. Description of Related Art

Nowadays, in addition to a hand held-type electronic device such as a smart phone and a tablet personal computer, a wearable-type electronic device, which a user is capable of wearing on the user's body, such as smart watches, smart glasses, and earbuds is also being actively developed.

The wearable electronic device may obtain user body information. For example, the wearable electronic device may obtain a user's biometric information through electrodes positioned in a part of an area in contact with the user's body. For example, the wearable electronic device may identify the biometric information using bioelectrical impedance analysis (BIA).

The wearable electronic device may exchange various signals with external devices. For example, the wearable electronic device may transmit and/or receive a signal to and/or from the outside through an antenna positioned in a part of a frame.

The above information is presented as background information to assist with an understanding of the disclosure. No determination has been made, and no assertion is made, as to whether any of the above might be applicable as prior art with regard to the disclosure.

A wearable electronic device may include an antenna formed by utilizing at least part of housing that forms an appearance. Moreover, the wearable electronic device may include at least one electrode in some of the remaining areas except for an area where an antenna of the housing is formed.

Because the wearable electronic device has limited arrangement space and housing size, there may be constraints that have restrictions in terms of aesthetics when the above-mentioned components are arranged.

Aspects of the disclosure address at least the above-mentioned problems and/or disadvantages and to provide at least the advantages described below.

SUMMARY

Embodiments of the disclosure provide a wearable electronic device that adaptively performs a communication function and a biometric information acquisition function may be provided by efficiently arranging an antenna and electrodes in the housing.

In accordance with an example embodiment of the disclosure, a wearable electronic device may include: a housing including a first surface forming a front surface of the wearable electronic device, a second surface facing away from the first surface, and a side surface surrounding an internal space between the first surface and the second surface, a first electrode area positioned in a part of the first surface and the side surface and including a plurality of electrodes, an antenna positioned in a part of the first surface and the side surface and divided through the first electrode area and a segment area, a display viewable through at least part of the first surface, a second electrode area positioned on the second surface, a processor, and a memory operatively connected to the processor and including instructions. For example, when executed by the processor, the instructions may cause the wearable electronic device to: obtain a biometric signal through the first electrode area, the second electrode area, or a combination of the first electrode area and the second electrode area based on a touch input to at least part of the first electrode area being detected, and perform wireless communication through the antenna.

In accordance with an example embodiment of the disclosure, a method in which a wearable electronic device obtains a biometric signal may include: identifying an electrical loop positioned on a first electrode, a second electrode, and a rear surface of the wearable electronic device and which is formed through a third electrode and a fourth electrode in contact with a part of a body of a user, or a combination of the third electrode and the fourth electrode based on a touch input to at least part of a first electrode and a second electrode positioned in a part of a front surface and a side surface of the wearable electronic device being detected, identifying biometric information based on a biometric signal obtained based on the electrical loop, and performing wireless communication through an antenna divided through the first electrode, the second electrode, and a segment area. For example, the first electrode and the second electrode may be spaced from each other through a first segment.

Other aspects, advantages, and salient features of the disclosure will become apparent to those skilled in the art from the following detailed description, which, taken in conjunction with the annexed drawings, discloses various example embodiments of the disclosure.

BRIEF DESCRIPTION OF THE DRAWINGS

The above and other aspects, features, and advantages of certain embodiments of the present disclosure will be more apparent from the following detailed description, taken in conjunction with the accompanying drawings, in which.

With regard to description of drawings, the same or similar components will be marked by the same or similar reference signs.

DETAILED DESCRIPTION

Hereinafter, various example embodiments of the disclosure will be described with reference to accompanying drawings. However, those of ordinary skill in the art will recognize that various modifications, equivalents, and/or alternatives of various example embodiments described herein may be variously made without departing from the scope and spirit of the disclosure.

Figure 1:
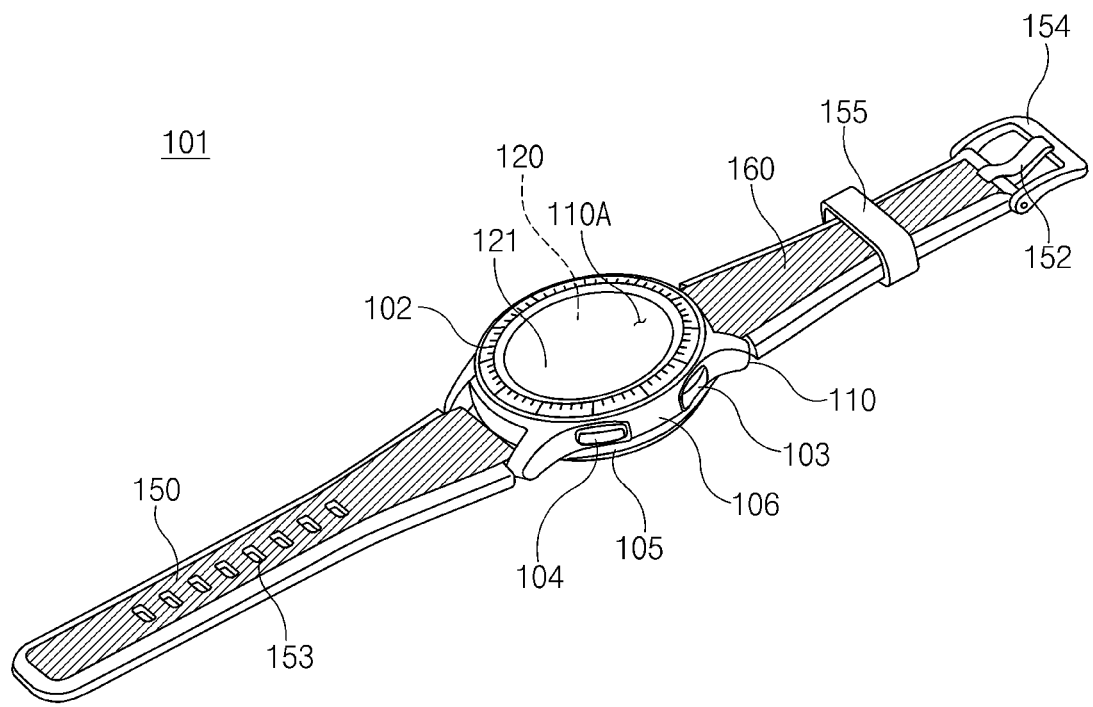
FIG. 1 is a front perspective view of an electronic device, according to various embodiments.

FIG. 1 is a front perspective view of an electronic device, according to various embodiments.

Figure 2:
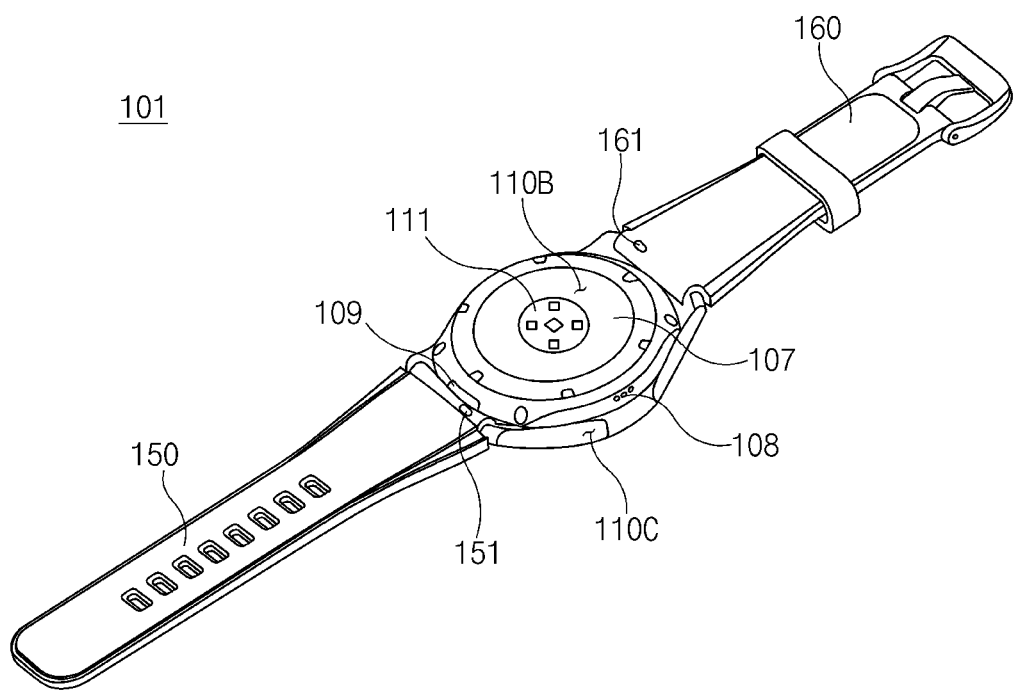
FIG. 2 is a rear perspective view of an electronic device according to various embodiments.

FIG. 2 is a rear perspective view of an electronic device, according to various embodiments.

Referring to FIGS. 1 and 2, an electronic device 101 according to an embodiment may include housing 110 including a first surface (or a front surface) 110A, a second surface (or a rear surface) 110B, and a side surface 110C surrounding a space between the first surface 110A and the second surface 110B, and binding members 150 and 160 connected to at least part of the housing 110 and configured to detachably bind the electronic device 101 to a body part (e.g., a wrist or an ankle) of a user. In an embodiment (not illustrated), the housing 110 may be referred to as a "structure" that forms a portion of the first surface 110A of FIG. 1, the second surface 110B of FIG. 2, and the side surface 110C of FIG. 2.

According to an embodiment, the first surface 110A may be implemented with a front plate 121 (e.g., a glass plate including various coating layers, or a polymer plate), at least a portion of which is substantially transparent. The second surface 110B may be formed by a rear plate 107 that is substantially opaque. For example, the rear plate 107 may be formed of a coated or colored glass, a ceramic, a polymer, a metal (e.g., aluminum, stainless steel (STS), or magnesium), or the combination of at least two of the materials. The side surface 111C may be coupled to the front plate 121 or the rear plate 107 and may be implemented with a side bezel structure (or a "side member") 106 including metal and/or polymer. In an embodiment, the rear plate 107 and the side bezel structure 106 may be integrally formed and may include the same material (e.g., a metal material such as aluminum).

The binding members (e.g., straps) 150 and 160 may be formed in various materials and shapes. The binding members 150 and 160 may be formed such that the integral type and a plurality of unit links are capable of being moved with each other by woven fabric, leather, rubber, urethane, metal, ceramic, or the combination of at least two of the materials.

According to an embodiment, the electronic device 101 may include at least one or more of a display 120, audio modules 105 and 108, a sensor module 111, key input devices 102, 103, and 104, and a connector hole 109. In an embodiment, the electronic device 101 may not include at least one (e.g., the key input device 102, 103, or 104, the connector hole 109, or the sensor module 111) of the components or may further include any other component.

For example, the display 120 may be visible through a substantial portion of the front plate 121. The shape of the display 120 may be a shape corresponding to the shape of the front plate 121, and may have various shapes such as a circle, an ellipse, or a polygon. The display 120 may be coupled to a touch sensing circuit, a pressure sensor capable of measuring the intensity (or pressure) of a touch, and/or a fingerprint sensor or may be disposed adjacent thereto.

The audio modules 105 and 108 may include the microphone hole 105 and the speaker hole 108. A microphone for obtaining external sound may be positioned within the microphone hole 105. In an embodiment, a plurality of microphones may be positioned to detect a direction of sound. The speaker hole 108 may be used as an external speaker and a call receiver. In an embodiment, the speaker hole 108 and the microphone hole 105 may be implemented with one hole, or a speaker (e.g., a piezoelectric speaker) may be included without the speaker hole 108.

The sensor module 111 may generate an electrical signal or a data value that corresponds to an internal operation state of the electronic device 101 or an external environment state. The sensor module 111 may include, for example, the sensor module 111 (e.g., a heart rate monitor (HRM) sensor) positioned on the second surface 110B of the housing 110. The electronic device 101 may further include a sensor module not illustrated, for example, at least one of a gesture sensor, a gyro sensor, a barometric pressure sensor, a magnetic sensor, an acceleration sensor, a grip sensor, a color sensor, an infrared (IR) sensor, a biometric sensor, a temperature sensor, a humidity sensor, or an illumination sensor.

The key input devices 102, 103, and 104 may include the wheel key 102 positioned on the first surface 110A of the housing 110 and rotatable in at least one direction and/or side key buttons 103 and 104 positioned on the side surface 110C of the housing 110. The wheel key 102 may have a shape corresponding to the shape of the front plate 121. In an embodiment, the electronic device 101 may not include all or a part of the key input devices 102, 103, and 104 mentioned above, and the key input devices 102, 103, and 104 not included may be implemented on the display 120 in a form such as a soft key. For example, the wheel key 102 may be implemented in a form that is operated based on a touch signal input to the display 120 (e.g., a wheel key area 302 of FIG. 3).

The connector hole 109 may include another connector hole (not illustrated) capable of accommodating a connector (e.g., a USB connector) for transmitting/receiving power and/or data to/from an external electronic device and accommodating a connector for transmitting/receiving an audio signal to/from the external electronic device. For example, the electronic device 101 may further include a connector cover (not illustrated) that covers at least part of the connector hole 109 and blocks the inflow of external foreign substances to the connector hole.

The binding members 150 and 160 may be detachably bound to at least a partial area of the housing 110, using locking members 151 and 161. The binding members 150 and 160 may include one or more of a fixing member 152, a fixing member fastening hole 153, a band guide member 154, and a band fixing ring 155.

The fixing member 152 may be configured to fix the housing 110 and the binding members 150 and 160 to the user's body part (e.g., a wrist or an ankle). The fixing member fastening hole 153 may fix the housing 110 and the binding members 150 and 160 to the user's body part in compliance with the fixing member 152. The band guide member 154 may be configured to limit the motion range of the fixing member 152 when the fixing member 152 is fastened with the fixing member fastening hole 153, and thus may allow the binding members 150 and 160 to be bound to the user's body part while being in close contact. In a state where the fixing member 152 is fastened to the fixing member fastening hole 153, the band fixing ring 155 may limit the motion range of the binding members 150 and 160.

Figure 3:
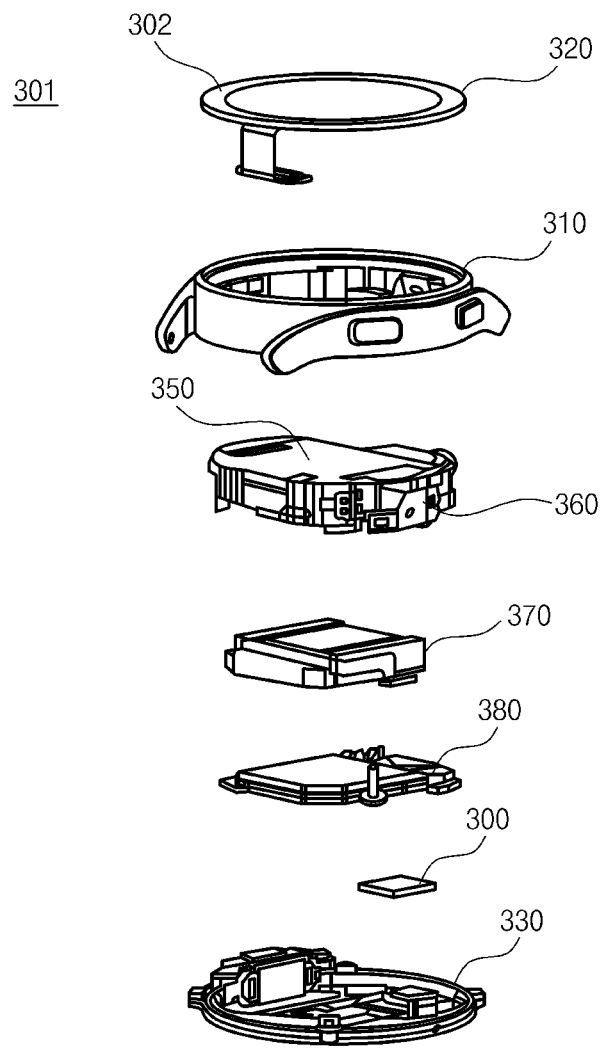
FIG. 3 is an exploded perspective view of an electronic device, according to various embodiments.

FIG. 3 is an exploded perspective view of an electronic device according to various embodiments. Referring to FIG. 3, an electronic device 301 (e.g., the electronic device 101 of FIG. 1) may include a display 320, a frame 310, an antenna 350, a support member 360 (e.g., a bracket), a battery 370, a printed circuit board 380, a back cover 330, and a biometric sensor module (e.g., including various sensor circuitry) 300. At least one of the components of the electronic device 301 may be identical or similar to at least one of the components of the electronic device 101 of FIG. 1 or 2, and thus, additional description may not be provided to avoid redundancy. According to an embodiment, the electronic device 301 may include at least part of components of the electronic device 101 of FIGS. 1 and 2. For example, the electronic device 301 according to an embodiment may include binding members 150 and 160 that are not shown.

In an embodiment, the display 320 (e.g., the display 120 of FIG. 1) may be at least partially accommodated in the frame 310. The display 320 may include the wheel key area 302 formed at an edge of the display 320. The wheel key area 302 may be configured to receive a user's touch input. The electronic device 301 according to an embodiment may perform a function substantially the same as a function performed through the wheel key 102 of FIG. 1 based on a touch input received through the wheel key area 302. In this case, the wheel key 102 thus physically implemented may be omitted.

In an embodiment, the frame 310 (e.g., the side surface bezel structure 106 of FIG. 1) may form the exterior (e.g., the side surface 110C of FIG. 1) of the electronic device 301. In an embodiment, the frame 310 may provide a space in which various components of the electronic device 301 are arranged or accommodated. For example, the display 320 may be disposed on one side of the frame 310, and the back cover 330 may be coupled to the other side of the frame 310. The antenna 350, the support member 360, the battery 370, the printed circuit board 380, and the biometric sensor module 300 may be positioned in the space defined by the frame 310, the display 320, and the back cover 330. In an embodiment, at least part of the display 320 (or the front plate 121 in FIG. 1), the frame 310, and/or the back cover 330 may be referred to as "housing" (e.g., the housing 110 in FIG. 1) of the electronic device 301 in that the at least part forms the exterior of the electronic device 301 and provides a space for accommodating various components of the electronic device 301.

In an embodiment, the support member 360 may be positioned inside the electronic device 301 to be connected to the frame 310 or may be integrally formed with the frame 310. For example, the support member 360 may be formed of a metal material and/or a nonmetal material (e.g., polymer). The display 320 may be coupled to one surface of the support member 360, and the printed circuit board 380 may be coupled to the other surface of the support member 360.

In an embodiment, a processor, a memory, and/or an interface may be mounted on the printed circuit board 380. The processor may include, for example, one or more of a central processing unit, an application processor, a graphic processing device, a sensor processor, or a communication processor. The memory may include, for example, a volatile memory or a nonvolatile memory. The interface may include, for example, a high definition multimedia interface (HDMI), a universal serial bus (USB) interface, a secure digital (SD) card interface, and/or an audio interface. The interface may electrically or physically connect, for example, the electronic device 301 with an external electronic device and may include a USB connector, an SD card/MMC connector, or an audio connector.

In an embodiment, the battery 370 that is a device for supplying power to at least one component of the electronic device 301 may include, for example, a rechargeable (secondary) battery. The battery 370 may be integrally disposed within the electronic device 301 or may be disposed to be removable from the electronic device 301.

In an embodiment, the antenna 350 may be positioned between the display 320 and the support member 360. The antenna 350 may include, for example, a near field communication (NFC) antenna, an antenna for wireless charging, and/or a magnetic secure transmission (MST) antenna. For example, the antenna 350 may perform short-range communication with an external device or may wirelessly transmit/receive power necessary for charging, and may transmit a short-range communication signal or a magnetic-based signal including payment data.

In an embodiment, the housing of the electronic device 301 may at least partially form an antenna for wireless communication. For example, an antenna may be formed by a part of the frame 310 and/or the support member 360 or a combination thereof. For another example, at least part of the antenna may be formed by a part of the frame 310 and/or the back cover 330 or a combination thereof. For example, at least part of the housing may be formed of a conductive member (e.g., metal). The housing may include at least one segment, of which at least part is formed of a non-conductive member, and may include at least one conductive area electrically segmented through at least one segment. In this case, the at least one conductive area may be used as an antenna (e.g., a radiator) that is electrically connected to a wireless communication circuit (e.g., a communication module 1990 of FIG. 19) included in the electronic device 301 and operates in at least one specified frequency band. In an embodiment, the electronic device 301 may perform, for example, cellular communication, short-range wireless communication such as Wi-Fi and Bluetooth, or may receive a global positioning system (GPS) signal through the antenna.

In an embodiment, the biometric sensor module 300 may be positioned between the printed circuit board 380 and the back cover 330. In an embodiment, the biometric sensor module 300 may at least partially face the back cover 330. For example, while a user wears the electronic device 301, the biometric sensor module 300 may be positioned to face the back cover 330 at least partially in contact with the user's wrist. In an embodiment, the biometric sensor module 300 may include at least one sensor configured to obtain biometric information (e.g., a heart rate, blood oxygen saturation, or a body temperature) of the user.

Figure 4:
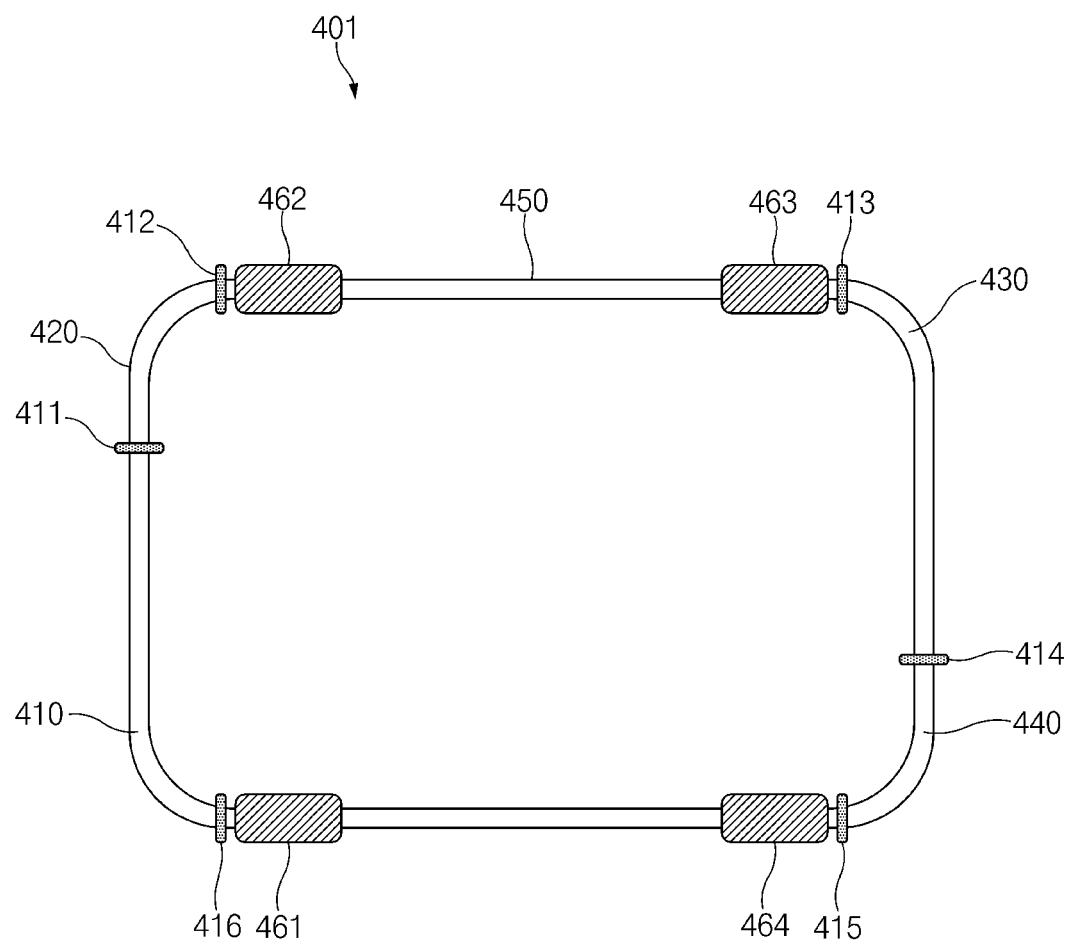
FIG. 4 is a diagram illustrating an example frame structure of an electronic device, according to various embodiments.

FIG. 4 is a diagram illustrating an example frame structure of an electronic device 401, according to various embodiments.

The electronic device 401 illustrated in FIG. 4 may be a smart phone, but embodiments of the disclosure are not limited thereto. For example, the electronic device according to various embodiments of the disclosure may be a wearable electronic device. A frame structure of a wearable electronic device according to an embodiment may be described in greater detail below with reference to FIGS. 5 to 7. FIG. 4 illustrates a frame structure of the electronic device 401, according to various embodiments. For example, segments 411, 412, 413, 414, 415, and 416 shown in FIG. 4 are conceptually shown. It may be understood that the segments 411, 412, 413, 414, 415 and 416 formed by physically separating housing 450 are present in at least part of the displayed portion. For another example, a plurality of electrodes 461, 462, 463, and 464 shown in FIG. 4 is a configuration thus conceptually illustrated. It may be understood that the electrodes are present in at least part of the displayed portion.

In an embodiment, the electronic device 401 may include an antenna formed in at least one area of the housing 450. For example, the electronic device 401 may include a plurality of antennas 410, 420, 430, and 440 divided through a segment area formed in a portion of a frame included in the housing 450. For example, the segment area may be defined as one area of the housing 450 including the segments 411, 412, 413, 414, 415 and 416.

For example, the electronic device 401 may include the first antenna 410 formed in an area, which is divided through the first segment 411 and the sixth segment 416, from among areas of the frame.

For example, the electronic device 401 may include the second antenna 420 formed in an area, which is divided through the first segment 411 and the second segment 412, from among areas of the frame.

For example, the electronic device 401 may include the third antenna 430 formed in an area, which is divided through the third segment 413 and the fourth segment 414, from among areas of the frame.

For example, the electronic device 401 may include the fourth antenna 440 formed in an area, which is divided through the fourth segment 414 and the fifth segment 415, from among areas of the frame.

In an embodiment, the electronic device 401 may include a plurality of electrode structures 461, 462, 463, and 464 positioned in at least one area of the housing 450. For example, the electronic device 401 may include the plurality of electrode structures positioned based on the segment areas formed in a part of a frame included in the housing 450.

For example, the electronic device 401 may include the first electrode 461 positioned in one area of the frame adjacent to the sixth segment 416.

For example, the electronic device 401 may include the second electrode 462 positioned in one area of the frame adjacent to the second segment 412.

For example, the electronic device 401 may include the third electrode 463 positioned in one area of the frame adjacent to the third segment 413.

For example, the electronic device 401 may include the fourth electrode 464 positioned in one area of the frame adjacent to the fifth segment 415.

In an embodiment, the electronic device 401 may identify user biometric information using the plurality of electrodes 461, 462, 463, and 464. For example, when at least part of the user's body is in contact with the plurality of electrodes 461, 462, 463, and 464, the electronic device 401 may obtain a biometric signal through the plurality of electrodes 461, 462, 463, and 464 and may identify the user biometric information based on the obtained biometric signal.

The housing and frame structure of the electronic device 401 described above are examples, and embodiments of the disclosure are not limited thereto. For example, the electronic device 401 may further include a configuration (e.g., a segment or a non-conductive member) that is positioned between the first electrode 461 and the fourth electrode 464 and is used to electrically isolate the first electrode 461 and the fourth electrode 464. For example, the electronic device 401 may further include a configuration that is positioned between the second electrode 462 and the third electrode 463 and is used to electrically isolate the second electrode 462 and the third electrode 463. For another example, the electronic device 401 may further include at least one antenna and/or electrode, or may not include at least one of the plurality of antennas and/or electrodes described above.

Figure 5:
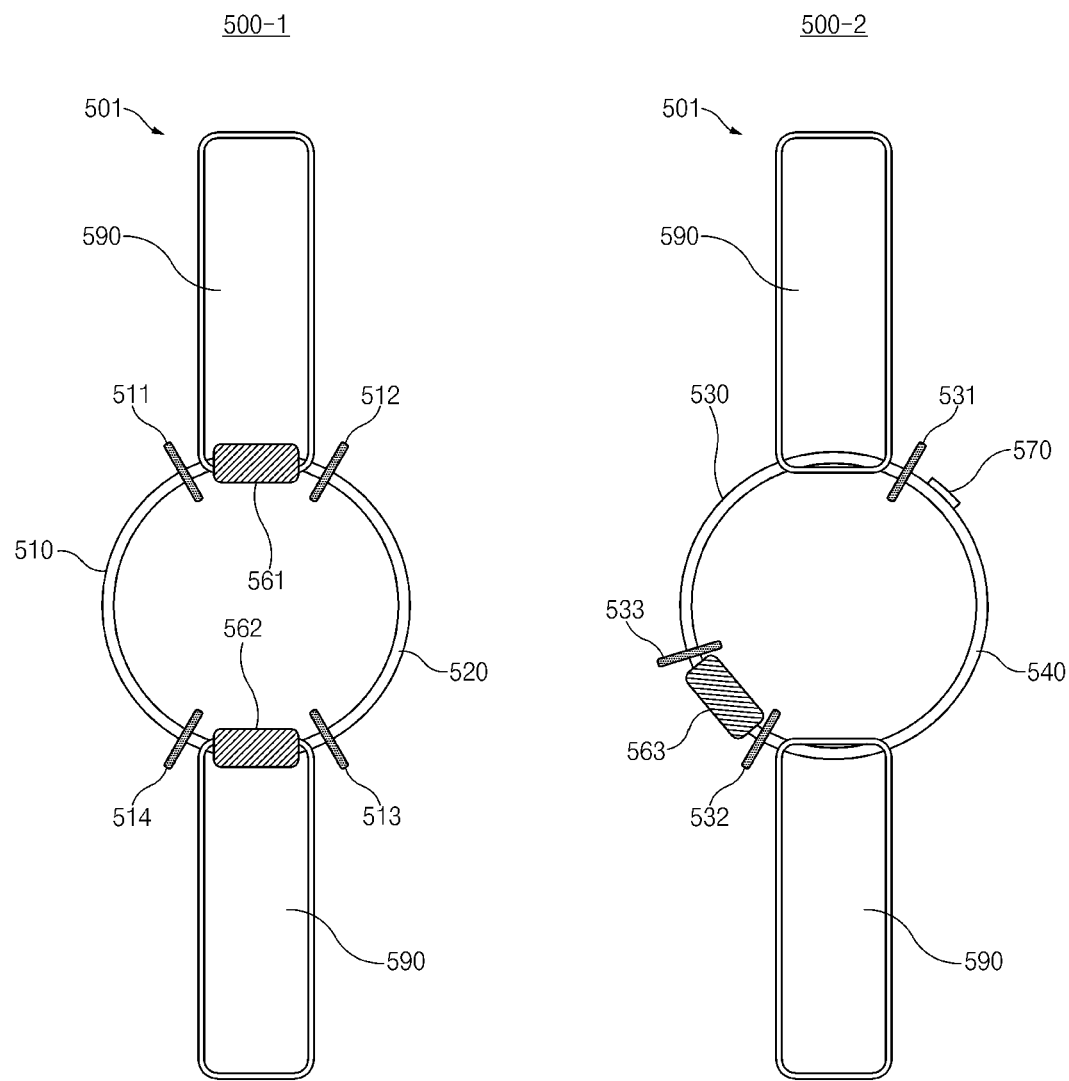
FIG. 5 is a diagram illustrating an example frame structure of an electronic device, according to various embodiments.

FIG. 5 is a diagram illustrating an example frame structure of an electronic device 501, according to various embodiments.

Figure 6:
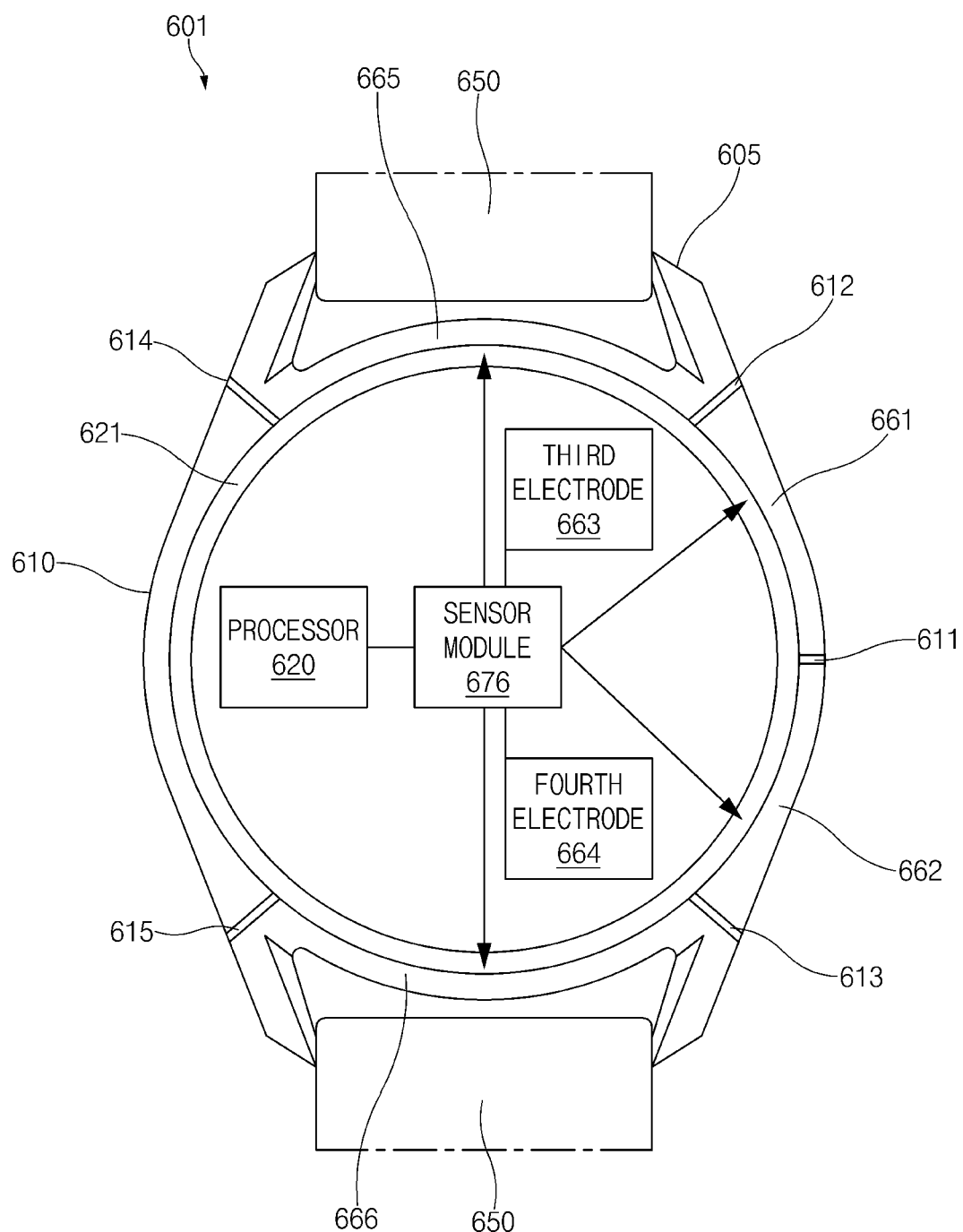
FIG. 6 is a diagram illustrating a front surface of an electronic device including an antenna and at least one electrode, according to various embodiments.
Figure 7:
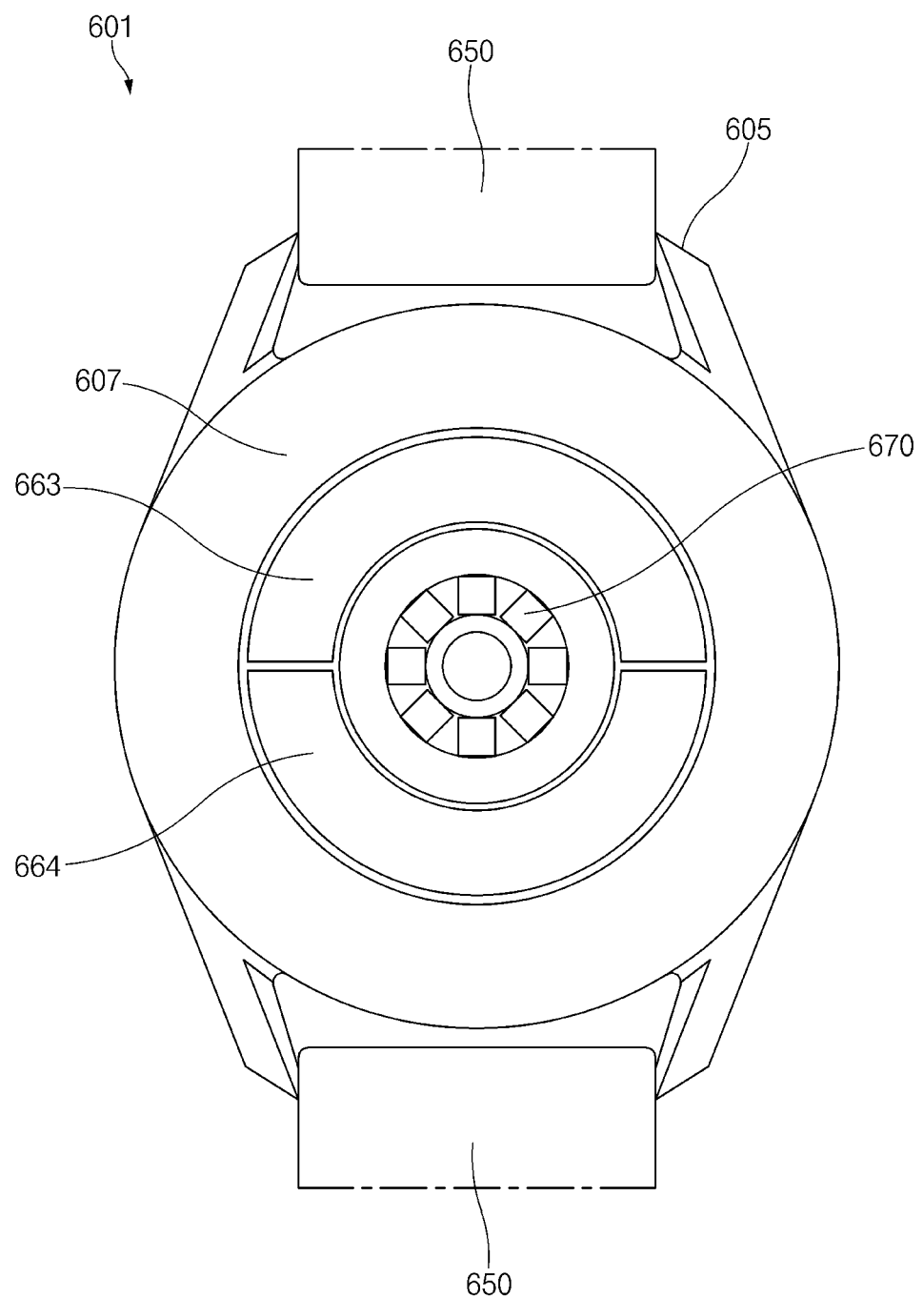
FIG. 7 is a diagram illustrating a rear surface of an electronic device including an antenna and at least one electrode, according to various embodiments.

According to an embodiment, an electronic device 501 illustrated in FIG. 5 may be a wearable electronic device capable being worn on a user's wrist. Moreover, the arrangement structure shown in FIG. 5 is a conceptual diagram schematically illustrating a configuration of the electronic device 501, and a more detailed embodiment is shown in FIGS. 6 and 7. FIG. 5 conceptually illustrates a frame structure of the electronic device 501, according to an embodiment of the disclosure. For example, segments 511, 512, 513, 514, 531, 532, and 533 shown in FIG. 5 are conceptually shown. It may be understood that the segments 511, 512, 513, 514, 531, 532 and 533 formed by physically separating housing are present in at least part of the displayed portion. For another example, a plurality of electrodes 561, 562, and 563 shown in FIG. 5 is a configuration thus conceptually illustrated. It may be understood that the electrodes are present in at least part of the displayed portion.

Referring to reference number 500-1, the electronic device 501 may include housing (e.g., at least part of the frame 310, the display 320, and/or the back cover 330 of FIG. 3) forming the exterior of the electronic device 501. For example, the electronic device 501 may include a binding member 590 (e.g., the binding members 150 and 160 in FIG. 1) that is bound to an area of the housing.

In an embodiment, the electronic device 501 may include a plurality of antennas 510 and 520 and the plurality of electrodes 561 and 562 formed or disposed in a portion of the housing. For example, the plurality of antennas 510 and 520 and the plurality of electrodes 561, 562, and 563 may be divided through segment areas formed in one area of the housing. For example, the segment area may be defined as one area of the housing including the segments 511, 512, 513, and 514.

For example, the first antenna 510 may be formed in one area of the housing divided through the first segment 511 and the fourth segment 514.

For example, the second antenna 520 may be formed in one area of the housing divided through the second segment 512 and the third segment 513.

For example, the first electrode 561 may be positioned in one area of the housing divided through the first segment 511 and the second segment 512.

For example, the second electrode 562 may be disposed in one area of the housing divided through the third segment 513 and the fourth segment 514.

Referring to reference number 500-2, the electronic device 501 may include housing forming the exterior of the electronic device 501. For example, the electronic device 501 may include the binding member 590 and a key input device 570 (e.g., the side key button 103 of FIG. 1) that are coupled to one area of the housing.

In an embodiment, the electronic device 501 may include a plurality of antennas 530 and 540 and at least one electrode, which are formed or positioned in a part of the housing. For example, the plurality of antennas 510 and 520 and the at least one electrode 563 may be divided through a segment area formed in one area of the housing. For example, the segment area may be defined as one area of the housing including the segments 531, 532, and 533.

For example, the third antenna 530 may be formed in one area of the housing divided through the fifth segment 531 and the seventh segment 533.

For example, the fourth antenna 540 may be formed in one area of the housing divided through the fifth segment 531 and the sixth segment 532.

For example, the third electrode 563 may be positioned in one area of the housing divided through the sixth segment 532 and the seventh segment 533.

In an embodiment, the electronic device 501 may identify user biometric information using the plurality of electrodes 561, 562, and 563. For example, when at least part of the user's body is in contact with the plurality of electrodes 561, 562, and 563, the electronic device 501 may obtain (or receive) a biometric signal through the plurality of electrodes 561, 562, and 563 and may identify the user biometric information based on the obtained (or received) biometric signal.

In an embodiment, the electronic device 501 may perform wireless communication with the outside using the plurality of antennas 510, 520, 530, and 540.

The housing and frame structure of the electronic device 501 described above are examples, and various embodiments of the disclosure are not limited thereto. For example, the electronic device 501 may further include at least one antenna and/or electrode, or may not include at least one of the plurality of antennas and/or electrodes described above.

FIG. 6 is a diagram illustrating a front surface of an electronic device 601 including an antenna 610 and at least one electrode 661, 662, 665, and/or 666, according to various embodiments.

FIG. 7 is a diagram illustrating a rear surface of an electronic device 601 including an antenna 610 and at least one electrode 663, 664, according to various embodiments.

Hereinafter, components included in an electronic device 601 (e.g., the electronic device 101 of FIG. 1) according to an embodiment illustrated in FIGS. 6 and 7 will be described based on a front plate 621 and a rear plate 607 included in housing 605. Moreover, a configuration indicating a processor (e.g., including processing circuitry) 620 and a sensor module 676 among components of the electronic device shown in FIG. 6 may be obtained by conceptually diagramming components positioned inside the housing 605. A configuration showing a third electrode 663 and a fourth electrode 664 among components of the electronic device shown in FIG. 6 may be obtained by conceptually diagramming components positioned on the rear plate 607.

According to an embodiment, the electronic device 601 may include the housing 605 forming the exterior of the electronic device 601. For example, the electronic device 601 may include a binding member 650 bound to an area of the housing 605.

In an embodiment, the electronic device 601 may include an antenna 610 and a plurality of electrodes 661, 662, 663, 664, 665, and 666 that are formed or positioned on a part of the housing 605. For example, the electronic device 601 may include a first electrode area that is disposed on a portion of the front plate 621 and a side surface (e.g., the side surface 110 of FIGS. 1 and 2) and includes a plurality of electrodes. The first electrode area may include the first electrode 661, the second electrode 662, the fifth electrode 665, and the sixth electrode 666. The antenna 610, the fifth electrode 665, and the sixth electrode 666 may be separated from one another through segment area (e.g., segments 614 and 615) formed in one area of the housing 605. For another example, the electronic device 601 may include a second electrode area disposed on the rear plate 607. The second electrode area may include the third electrode 663 and the fourth electrode 664.

For example, the plurality of electrodes 661, 662, 663, 664, 665, and 666 may be electrically connected to some (e.g., the sensor module 676) of components included in the electronic device 601 through at least one connection member (not shown) (e.g., a wire or conductive member).

For example, the electronic device 601 may include the first electrode 661 divided through a first segment 611 and a second segment 612 on the front plate 621 of the housing 605.

For example, the electronic device 601 may include the second electrode 662 divided through the first segment 611 and the third segment 613 on the front plate 621 of the housing 605.

For example, the electronic device 601 may include the fifth electrode 665 divided through the second segment 612 and the fourth segment 614 on the front plate 621 of the housing 605.

For example, the electronic device 601 may include the sixth electrode 666 divided through a third segment 613 and the fifth segment 615 on the front plate 621 of the housing 605.

For example, the electronic device 601 may include the antenna 610 divided through the fourth segment 614 and the fifth segment 615 on the front plate 621 of the housing 605. For example, the antenna 610 may be arranged spaced from the fifth electrode 665 through the fourth segment 614. For another example, the antenna 610 may be arranged spaced from the sixth electrode 666 through the fifth segment 615.

For example, the electronic device 601 may include the third electrode 663 and the fourth electrode 664 positioned on the rear plate 607 of the housing 605. For example, the third electrode 663 and the fourth electrode 664 may be physically spaced from each other through a segment area.

For example, the electronic device 601 may include an optical sensor 670 positioned on the rear plate 607 of the housing 605. For example, the optical sensor 670 may be included in the sensor module 676 and may further include an optical signal processing module (not shown) electrically connected to a light source and a plurality of photo detectors. The optical signal processing module may obtain and process a current signal generated based on the amount of light detected by a plurality of photo detectors. For example, the optical sensor 670 may include a photoplethysmogram (PPG) sensor. The optical signal processing module may detect a user's biometric information or may detect whether the user is wearing a wearable electronic device, using an electrical signal (e.g., a PPG signal) obtained through the plurality of photo detectors. The plurality of photo detectors may detect light and may sense the intensity of the detected light. For example, the plurality of photo detectors may output a current signal having a level corresponding to the detected amount of light. The plurality of photo detectors may be arranged to surround the light source. FIG. 6 illustrates that the electronic device 601 includes eight photo detectors. However, the number and/or locations of the photo detectors according to embodiments of the disclosure are not limited thereto. The light source may include at least one light emitting element (e.g., a light emitting diode (LED)) for irradiating light having a wavelength in a specified range. For example, each light emitting element may be configured to emit light of different wavelengths. For another example, at least part of the light emitting elements may be configured to emit light of the same wavelength. For another example, each light emitting element may emit light at the same time point or may emit light based on a specified pattern.

In an embodiment, when a touch input to at least part of a plurality of electrodes is detected while the electronic device 601 is worn on a part of the user's body (e.g., a wrist), the electronic device 601 may obtain a biometric signal through electrodes, at each of which the touch input is detected. For example, when the touch input to at least part of the first electrode area is detected, the electronic device 601 may obtain a biometric signal through the first electrode area, the second electrode area, or a combination thereof. For example, when a touch input to at least part of the first electrode 661 and the second electrode 662 in the first electrode area is detected, the electronic device 601 may identify an electrical loop formed through the first electrode 661, the second electrode 662, the third electrode 663, the fourth electrode 664, or a combination thereof, and may identify biometric information associated with the user based on the biometric signal that is obtained based on the electrical loop.

For example, when a touch input to at least part of a plurality of electrodes is detected, the electronic device 601 may provide haptic feedback to an electrode area in which the touch input is detected. For example, the electronic device 601 may include at least one haptic module positioned at a location corresponding to each electrode area. When a touch input is detected, the electronic device 601 may provide haptic feedback using a haptic module positioned at a location corresponding to an electrode area in which the touch input is detected.

For example, when a first touch input to the first electrode 661 is detected, the electronic device 601 may identify a first electrical loop formed through the first electrode 661, the third electrode 663, and the fourth electrode 664 and may identify electrocardiogram (ECG) information of the user wearing the electronic device 601 based on an ECG signal obtained based on the first electrical loop.

For example, when a second touch input to an area including the first electrode 661, the second electrode 662, and the first segment 611 is detected, the electronic device 601 may obtain an ECG signal using the first electrode 661 having low contact impedance among the first electrode 661 and the second electrode 662. While obtaining the ECG signal using the first electrode 661, the electronic device 601 may turn off the operation of the second electrode 662.

For example, when a third touch input to an area including the first electrode 661 and the second electrode 662 is detected, the electronic device 601 may identify a second electrical loop formed through the first electrode 661, the second electrode 662, the third electrode 663, and the fourth electrode 664 and may identify the user's body information based on a BIA signal obtained based on the second electrical loop. For example, when it is identified that only the touch input to the first electrode 661 is detected while the electronic device 601 obtains the BIA signal, the electronic device 601 may display guide information associated with the operation state of the second electrode 662 on a display (e.g., the display 120 in FIG. 1) viewable through at least part of the front plate 621.

For example, when a fourth touch input to an area including the first electrode 661, the second electrode 662, the first segment 611, the third segment 613, and the sixth electrode 666 is detected, the electronic device 601 may obtain the BIA signal using the first electrode 661 and the second electrode 662, which has low contact impedance, from among the second electrode 662 and the sixth electrode 666. While the electronic device 601 obtains the BIA signal using the first electrode 661 and the second electrode 662, the electronic device 601 may turn off operations of the fifth electrode 665 and the sixth electrode 666. For example, the electronic device 601 may further include a switch (not shown) (e.g., the switch 910 of FIG. 9) electrically connected to a plurality of electrodes. The electronic device 601 may turn off an operation of at least part of the plurality of electrodes by cutting off an electrical connection between the at least part of the plurality of electrodes and a circuit (e.g., a BIA circuit (e.g., a BIA circuit 920) or an ECG circuit (e.g., an ECG circuit 930) in FIG. 9) for biometric information identification, or may identify biometric information of the user wearing the electronic device 601 by activating the electrical connection. For example, while obtaining the BIA signal using the first electrode 661 and the second electrode 662, the electronic device 601 may turn off operations of the fifth electrode 665 and the sixth electrode 666 by cutting off electrical connections with the fifth electrode 665 and the sixth electrode 666 through a switch.

For example, the electronic device 601 may display a user interface related to operation states of a plurality of electrodes on a display. For example, while obtaining the BIA signal using the first electrode 661 and the second electrode 662, the electronic device 601 may display a user interface indicating that the first electrode 661 and the second electrode 662 are turned on, on the display. When a specified input to the user interface is detected, the electronic device 601 may change at least one operation state among the first electrode 661, the second electrode 662, the fifth electrode 665, or the sixth electrode 666. For example, the specified input may refer to a touch input for turning off the first electrode 661 and the second electrode 662 and turning on the fifth electrode 665 and the sixth electrode 666. In this case, the electronic device 601 may turn off the first electrode 661 and the second electrode 662 and may turn on the fifth electrode 665 and the sixth electrode 666. For example, the electronic device 601 may turn off the first electrode 661 and the second electrode 662 by cutting off electrical connections with the first electrode 661 and the second electrode 662 through a switch. Furthermore, the electronic device 601 may turn on the fifth electrode 665 and the sixth electrode 666 by activating electrical connections with the fifth electrode 665 and the sixth electrode 666.

The above-described operation of the electronic device 601 of FIGS. 6 and 7 may refer to an operation performed by the processor 620 positioned in the electronic device 601. For example, the processor 620 may control a signal processing operation through a plurality of electrodes using the sensor module 676.

Figure 8:
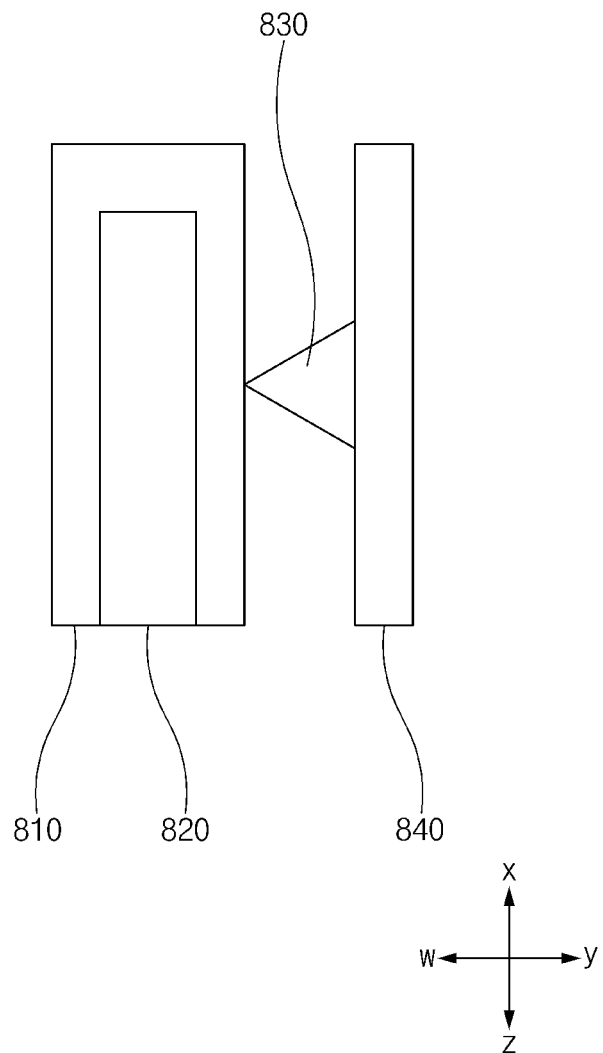
FIG. 8 is a diagram illustrating an example arrangement structure of an electronic device, according to various embodiments.

FIG. 8 is a diagram illustrating an example arrangement structure of an electronic device, according to various embodiments.

Hereinafter, a description of the arrangement structure of FIG. 8 will be described based on 'x' direction toward a rear plate (e.g., the rear plate 607 of FIG. 7) of an electronic device (e.g., the electronic device 601 of FIGS. 6 and 7), 'z' direction toward a front plate (e.g., the front plate 621 of FIG. 6) of the electronic device, 'y' direction toward an inside of housing (e.g., the housing 605 of FIGS. 6 and 7) of the electronic device, and 'w' direction toward an outside of the housing of the electronic device.

In an embodiment, a plurality of electrodes (e.g., the first electrode 661, the second electrode 662, the third electrode 663, the fourth electrode 664, the fifth electrode 665, and/or the sixth electrode 666 of FIG. 6) included in the electronic device may include a coating layer 810 and a body layer 820.

For example, the coating layer 810 may be formed of indium tin oxide (ITO), CrSiCN, or a combination thereof.

For example, the body layer 820 may be formed of ceramic, gorilla glass, or a combination thereof.

In an embodiment, each of the plurality of electrodes may be electrically connected to a PCB 840 positioned inside the housing through a connector 830 in contact with a part of the coating layer 810.

Figure 9:
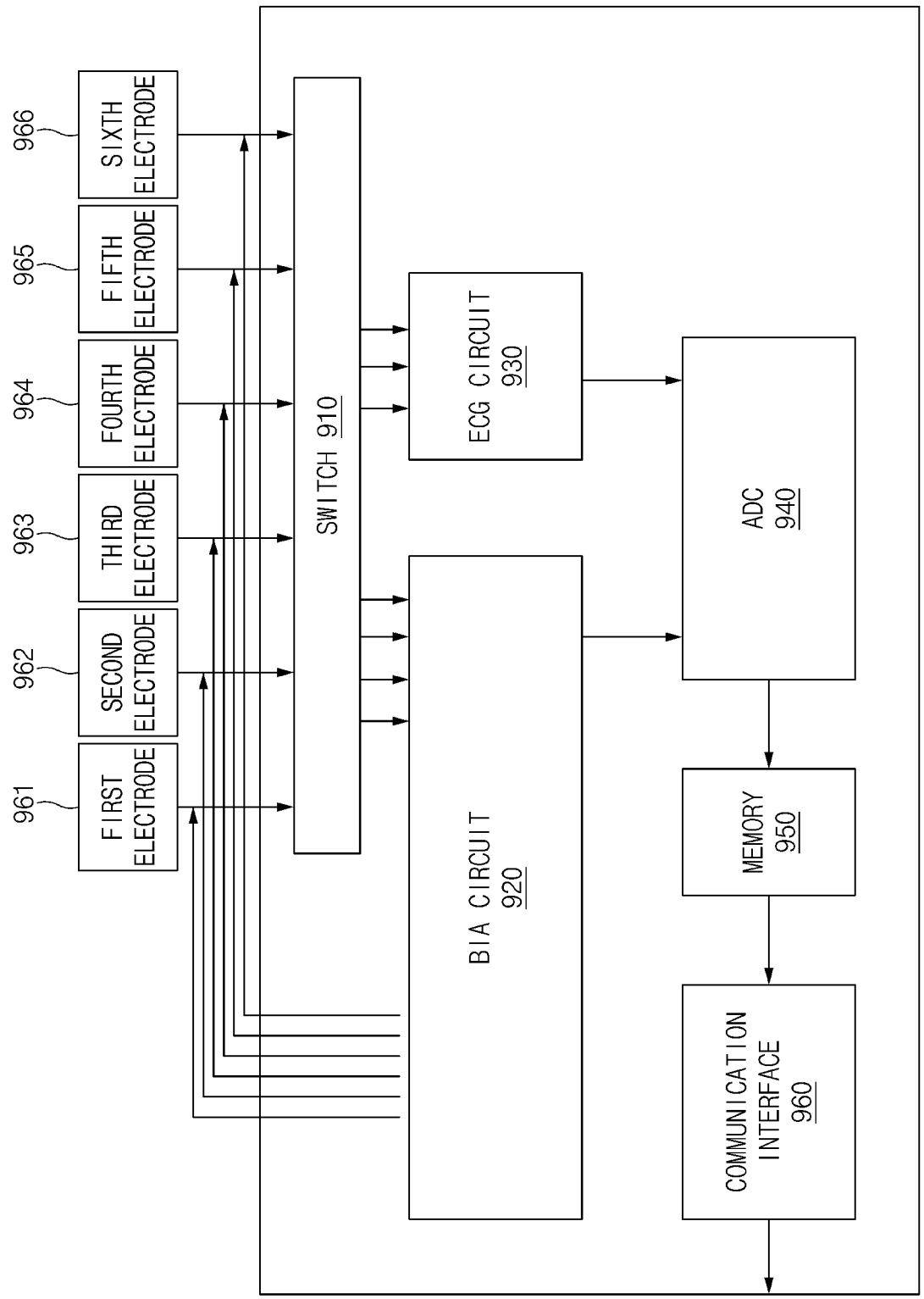
FIG. 9 is a block diagram illustrating example components included in an electronic device, according to various embodiments.

FIG. 9 is a block diagram illustrating various components included in an electronic device, according to various embodiments.

In FIG. 9, a description of a component having the same name as that of FIGS. 6 and 7 may be replaced with a description of a component included in the electronic device 601 (e.g., the electronic device 101 of FIG. 1) of FIGS. 6 and 7.

According to an embodiment, an electronic device may include a plurality of electrodes 961, 962, 963, 964, 965, and 966. For example, the plurality of electrodes may include a first electrode 961, a second electrode 962, a fifth electrode 965, and a sixth electrode 966 that are included in the first electrode area. The first electrode area may be positioned on a part of a front surface of the electronic device and a side surface surrounding an internal space between the front surface and a rear surface of the electronic device. For example, a plurality of electrodes may further include a third electrode 963 and a fourth electrode 964 included in the second electrode area. The second electrode area may be disposed on the rear surface of the electronic device.

Figure 19:
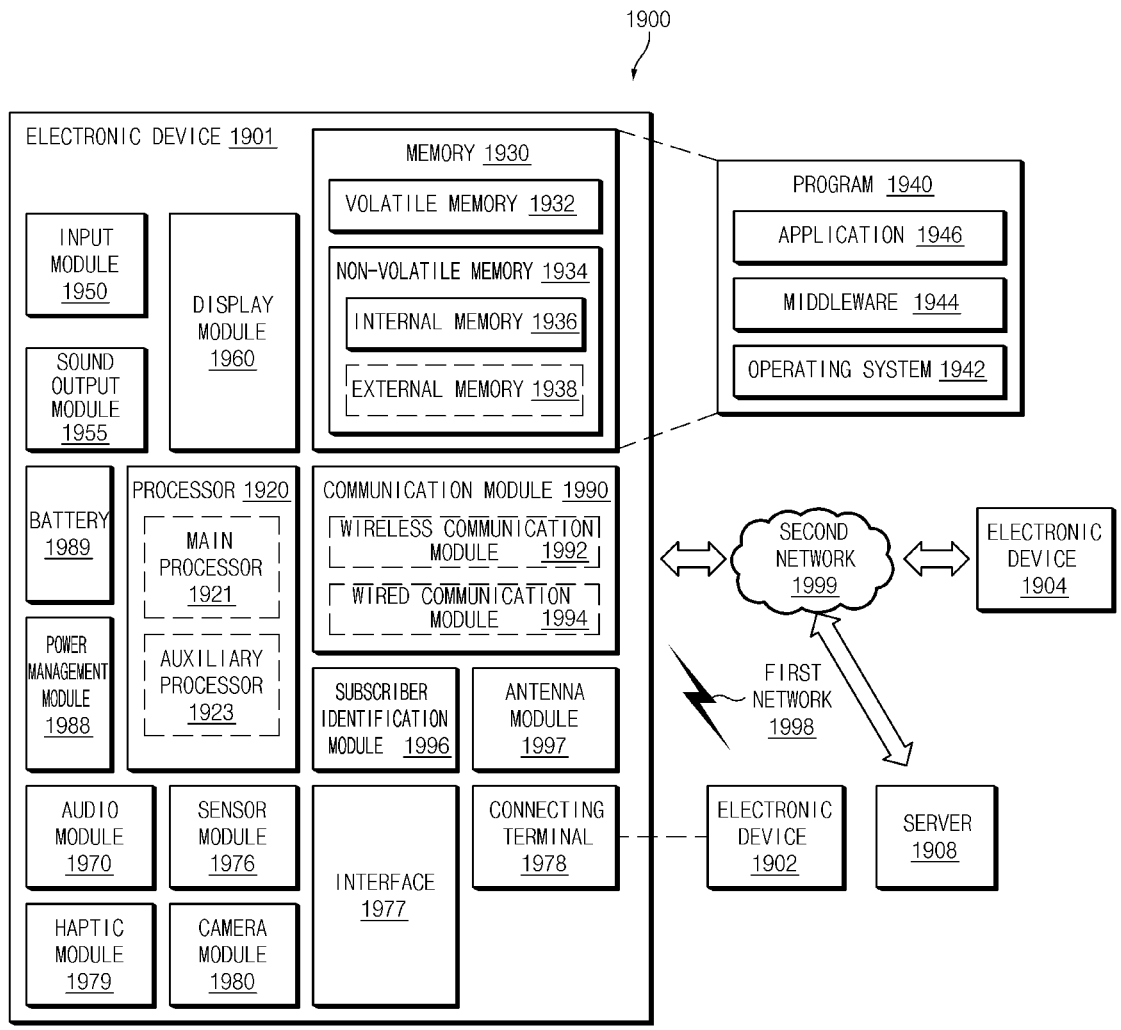
FIG. 19 is a block diagram illustrating an example electronic device in a network environment, according to various embodiments.

According to an embodiment, the electronic device may include a switch 910, a BIA circuit 920, an ECG circuit 930, an analog digital converter (ADC) 940, a memory 950 (e.g., the memory 1930 in FIG. 19), and a communication interface (e.g., including communication circuitry) 960 (e.g., the communication module 1990 of FIG. 19). The components shown in FIG. 9 are examples, and the electronic device may further include components not shown in FIG. 9. For example, the electronic device may further include a processor (e.g., the processor 1920 of FIG. 19) electrically connected to the communication interface 960. For another example, the electronic device may further include an antenna (e.g., the antenna 610 of FIG. 6). For example, the antenna may be arranged spaced from the plurality of electrodes 961, 962, 963, 964, 965 and 966 so as to be electrically isolated from the plurality of electrodes 961, 962, 963, 964, 965 and 966.

In an embodiment, the plurality of electrodes 961, 962, 963, 964, 965, and 966 may obtain a biometric signal. For example, the plurality of electrodes 961, 962, 963, 964, 965, and 966 may measure a BIA and/or an ECG of a user who wears the electronic device. For example, when a part (e.g., a finger) of the user's body is in contact with at least part of the plurality of electrodes 961, 962, 963, 964, 965, and 966, the electronic device may obtain a biometric signal using the contacted electrode. For example, the electronic device may obtain a biometric signal through a closed circuit formed through the first electrode 961 and the second electrode 962, which are in contact with a part of the user's body, and the third electrode 963 and the fourth electrode 964, which are in contact with the user's wrist.

In an embodiment, the electronic device may generate current using the BIA circuit 920 and may transmit the generated current to at least part of the plurality of electrodes 961, 962, 963, 964, 965 and 966. At least one electrode receiving the current and the user's body may form one closed circuit.

In an embodiment, the plurality of electrodes 961, 962, 963, 964, 965, and 966 may transmit the obtained biometric signal to the switch 910. For example, the biometric signal may include a voltage measured through the closed circuit.

In an embodiment, the switch 910 may selectively transmit the biometric signal received from the plurality of electrodes 961, 962, 963, 964, 965, and 966 to the outside. For example, the switch 910 may selectively transmit the biometric signal received from the plurality of electrodes 961, 962, 963, 964, 965, and 966 to the BIA circuit 920 or the ECG circuit 930 under the control of a processor (not shown).

In an embodiment, the BIA circuit 920 and the ECG circuit 930 may process the received biometric signal. For example, the BIA circuit 920 and the ECG circuit 930 may include a filter and/or an amplifier. For example, the BIA circuit 920 and the ECG circuit 930 may remove high-frequency noise included in the received biometric signal. For another example, the BIA circuit 920 and the ECG circuit 930 may amplify the received biometric signal. For example, the BIA circuit 920 may measure body impedance based on the received biometric signal. For example, the BIA circuit 920 and the ECG circuit 930 may transmit the processed biometric signal to the ADC 940.

In an embodiment, the ADC 940 may receive the processed biometric signal from the BIA circuit 920 and the ECG circuit 930. The ADC 940 may convert the received biometric signal into digital format data. For example, when the received biometric signal is a waveform obtained by measuring the user's BIA, the ADC 940 may convert the biometric signal into BIA measurement data. For example, when the received biometric signal is a waveform obtained by measuring the user's ECG, the ADC 940 may convert the biometric signal into ECG measurement data. For example, the ADC 940 may transmit data converted to a digital format to the memory 950.

In an embodiment, the memory 950 may store at least part of the data transmitted from the ADC 940. For example, the memory 950 may be a first-in first-out (FIFO) memory. For example, the memory 950 may transmit the at least part of data transmitted from the ADC 940 to the communication interface 960.

In an embodiment, the communication interface 960 may include various communication circuitry and transmit and/or receive electrical signals to and from the processor (not shown) based on an inter integrated circuit (I2C) communication or a serial peripheral interface (SPI) communication. For example, the communication interface 960 may transmit at least part of data received from the memory 950 to the processor.

Figure 10:
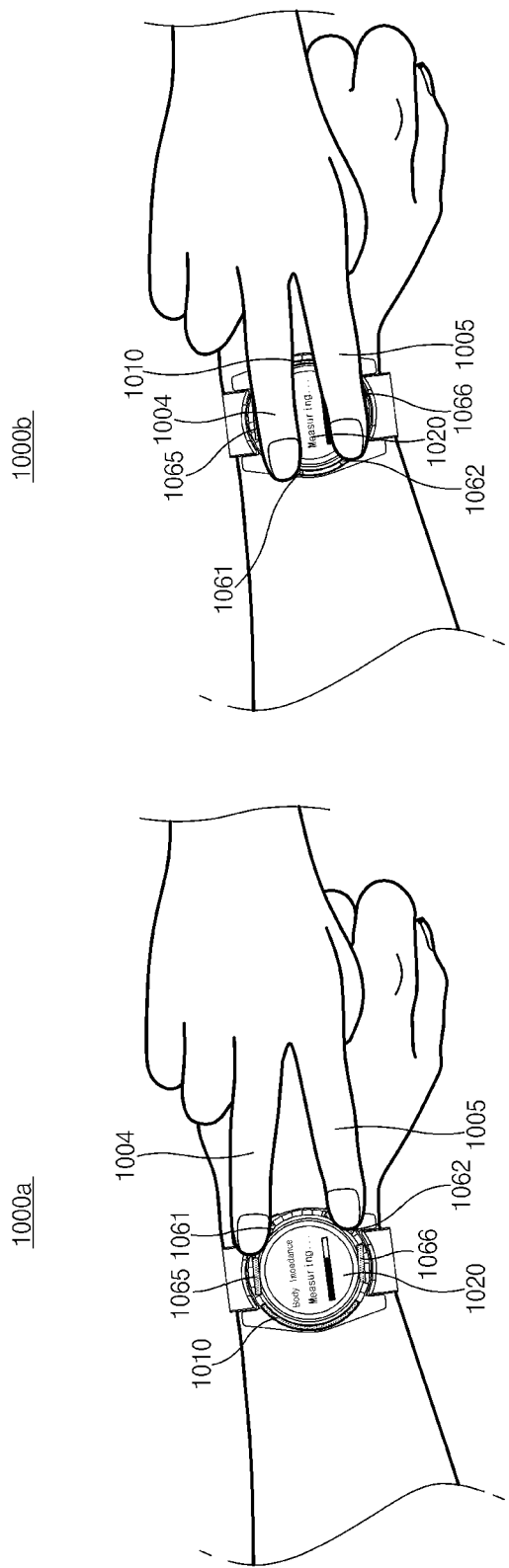
FIG. 10 is a diagram illustrating an example operation of an electronic device, according to various embodiments.

FIG. 10 is a diagram illustrating an example operation of an electronic device, according to various embodiments.

Reference numeral 1000*a* and reference numeral 1000*b* illustrate example arrangement structures of an electronic device (e.g., the electronic device 601 of FIG. 6) in which electrodes are positioned at different locations, respectively.

Referring to reference numeral 1000*a* and reference numeral 1000*b*, according to an embodiment, the electronic device may include a plurality of electrodes 1061, 1062, 1065, and 1066 and an antenna 1010 positioned on at least part of housing (e.g., the housing 605 of FIG. 6).

Referring to reference numeral 1000*a*, in an embodiment, the first electrode 1061 and the second electrode 1062 may be positioned on a right side based on a direction in which a display 1020 (e.g., the display 120 of FIG. 1) of the electronic device is viewed.

Referring to reference numeral 1000*b*, in an embodiment, the first electrode 1061 and the second electrode 1062 may be positioned on a left side based on the direction in which the display 1020 (e.g., the display 120 of FIG. 1) of the electronic device is viewed.

In an embodiment, while the electronic device is worn on at least part of a user's body, the electronic device may detect that a first portion 1004 and a second portion 1005 of the user's body are in contact with the first electrode 1061 and the second electrode 1062, respectively. The electronic device may identify the user's biometric information through an electrical loop formed through the first electrode 1061, the second electrode 1062, and a third electrode (e.g., the third electrode 663 of FIG. 7) and a fourth electrode (e.g., the fourth electrode 664 of FIG. 7) that are positioned on a rear plate (e.g., the rear plate 607 of FIG. 7).

In FIG. 10, in the case where the user applies a touch input to the first electrode 1061 and the second electrode 1062 using a part of a right hand, the user may receive biometric information more conveniently than the reference numeral 1000*b* because the user does not cover the display 1020 when the user employs the electronic device according to the arrangement structure of reference numeral 1000*a*. Although not shown in FIG. 10, in the case where the user applies a touch input to the first electrode 1061 and the second electrode 1062 using a part of a left hand, the user may receive biometric information while the user does not cover the display 1020 when the user employs the electronic device according to the arrangement structure of reference numeral 1000*b*. Accordingly, according to an embodiment of the disclosure, the electronic device may selectively turn on (or activate) a part of the plurality of electrodes according to the user's wearing type and/or touch input type or may display guide information for measuring biometric information, thereby providing intuitive and convenient usability.

Figure 11:
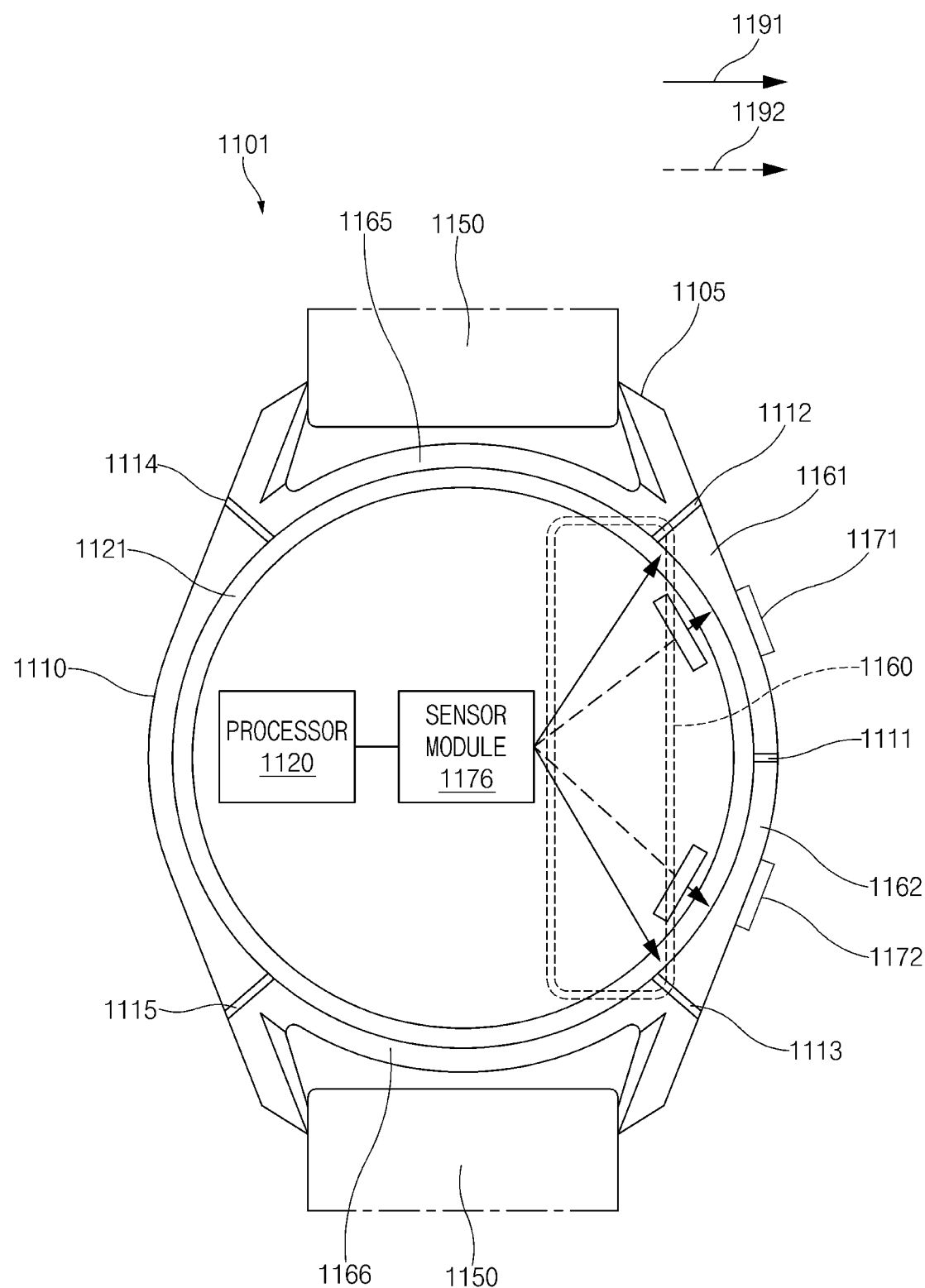
FIG. 11 is a diagram illustrating a front surface of an electronic device including an antenna and at least one electrode, according to various embodiments.

FIG. 11 is a diagram illustrating a front surface of an electronic device including an antenna and at least one electrode, according to various embodiments.

In FIG. 11, a description of a component having the same name as that of FIGS. 6 and 7 may be replaced with a description of a component included in the electronic device 601 of FIGS. 6 and 7. For example, descriptions of housing 1105, an antenna 1110, a first segment 1111, a second segment 1112, a third segment 1113, a fourth segment 1114, a fifth segment 1115, a processor 1120, a front plate 1121, a binding member 1150, a first electrode 1161, a second electrode 1162, a fifth electrode 1165, a sixth electrode 1166, and a sensor module 1176 of an electronic device 1101 may be replaced with descriptions of components included in the electronic device 601 of FIGS. 6 and 7. Hereinafter, the arrangement structure of the electronic device 1101 will be described below focusing on differences from FIGS. 6 and 7.

In an embodiment, the electronic device 1101 may further include a first key button 1171 and a second key button 1172, which are positioned on a side surface (e.g., the side surface 110C of FIG. 1) and include a structure extending toward the internal space of the housing 1105.

In an embodiment, the electronic device 1101 may obtain a biometric signal through the first electrode 1161, the second electrode 1162, the fifth electrode 1165, the sixth electrode 1166, the first key button 1171, the second key button 1172, or a combination thereof. For example, an electrical path between the sensor module 1176 and the first electrode 1161, and an electrical path between the sensor module 1176 and the second electrode 1162 may be referred to as "reference numeral 1191". For another example, an electrical path between the sensor module 1176 and the first key button 1171, and an electrical path between the sensor module 1176 and the second key button 1172 may be referred to as "reference numeral 1192".

In an embodiment, the electronic device 1101 may further include a ground shielding area 1160 for electrically isolating an electrode and a key button. For example, the electronic device 1101 may include the ground shielding area 1160 for electrically isolating a signal line through an electrode and a signal line through a key button from each other. For example, a description of a structure of the ground shielding area 1160 may be referenced in more detail in the circuit diagram of FIG. 12 to be described in greater detail below.

Figure 12:
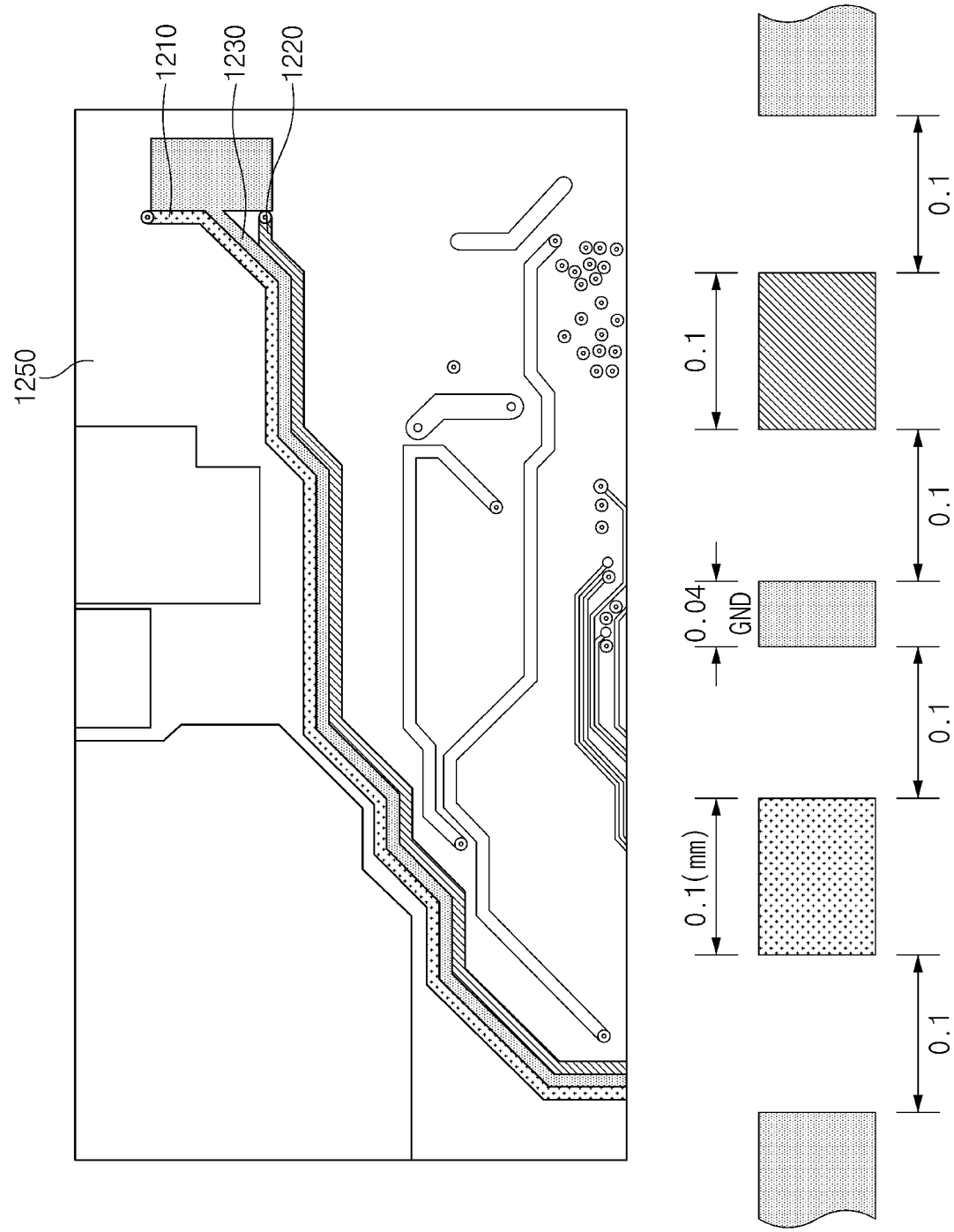
FIG. 12 is a diagram illustrating an area of a circuit structure positioned in an electronic device, according to various embodiments.

FIG. 12 is a diagram illustrating an area of a circuit structure positioned in an electronic device, according to various embodiments.

In an embodiment, the electronic device 1101 may include a PCB 1250 positioned inside the housing 1105.

In an embodiment, a first signal line 1210 (e.g., a BIA signal transmission/reception line) and a second signal line 1220 (e.g., an ECG signal transmission/reception line) may be positioned on the PCB 1250.

For example, each of the first signal line 1210 and the second signal line 1220 may have a thickness of about 0.1 mm, but this is an example. Embodiments of the disclosure are not limited thereto.

In an embodiment, a ground shielding area 1230 may be positioned between the first signal line 1210 and the second signal line 1220.

For example, the thickness of the ground shielding area 1230 may be about 0.04 mm, but this is an example. Embodiments of the disclosure are not limited thereto.

For example, a separation distance between the first signal line 1210 and the ground shielding area 1230 may be about 0.1 mm. For another example, a separation distance between the second signal line 1220 and the ground shielding area 1230 may be about 0.1 mm. The above-described numerical values are examples and embodiments of the disclosure are not limited thereto.

FIG. 12 illustrates that the ground shielding area 1230 is positioned between the first signal line 1210 and the second signal line 1220, but embodiments of the disclosure are not limited thereto. For example, the ground shielding area may be additionally positioned on the PCB 1250 in at least part of an area adjacent to the first signal line 1210 and/or the second signal line 1220.

Figure 13:
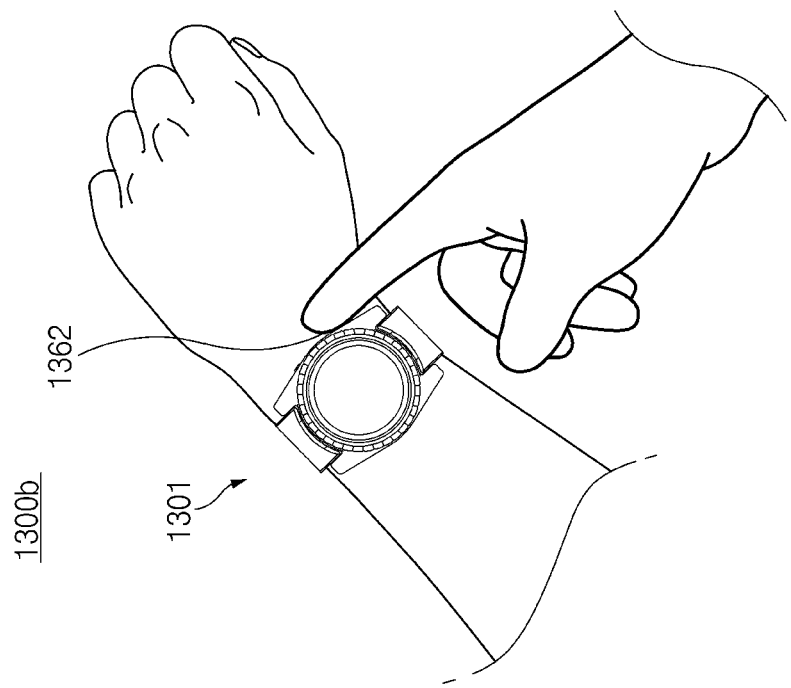
FIG. 13 is a diagram illustrating an example operation of an electronic device, according to various embodiments.
Figure 13:
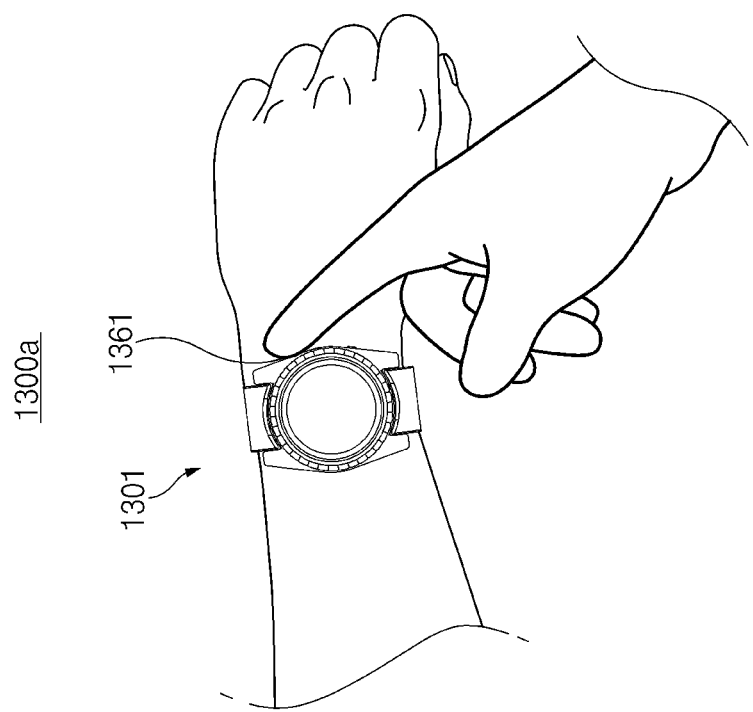

FIG. 13 is a diagram illustrating an example operation of an electronic device 1301, according to various embodiments.

FIG. 13 may show an operation of the electronic device 1301 identifying a user's ECG information using one electrode among a plurality of electrodes (e.g., the first electrode 661, the second electrode 662, the fifth electrode 665, and the sixth electrode 666 of FIG. 6) in a first electrode area positioned on a part of a front plate (e.g., the front plate 621 of FIG. 6) and a side surface (e.g., the side surface 110C of FIG. 1).

According to an embodiment, when a touch input to one of a plurality of electrodes included in the first electrode area is detected in a state where the electronic device 1301 is worn by the user, the electronic device 1301 may identify user biometric information through an electrode where the touch input is detected, while the touch input continues.

Referring to reference numeral 1300a, in an embodiment, when a touch input to a first electrode 1361 (e.g., the first electrode 661 of FIG. 6) among a plurality of electrodes is detected, the electronic device 1301 may obtain a biometric signal through the first electrode 1361.

For example, the electronic device 1301 may identify an electrical loop formed through the first electrode 1361, a third electrode (e.g., the third electrode 663 of FIG. 7) and a fourth electrode (e.g., the fourth electrode 664 of FIG. 7) which are positioned within the second electrode area positioned on a rear plate (e.g., the rear plate 607 of FIG. 7), and may identify the user's ECG information based on the ECG signal obtained based on the electrical loop.

Referring to reference numeral 1300b, in an embodiment, when a touch input to a second electrode 1362 (e.g., the second electrode 662 of FIG. 6) among the plurality of electrodes is detected, the electronic device 1301 may obtain a biometric signal through the second electrode 1362.

For example, the electronic device 1301 may identify an electrical loop formed through the second electrode 1362, a third electrode positioned on the rear plate, a fourth electrode positioned on the rear plate, and the first electrode 1361 and may identify the user's ECG information based on the ECG signal obtained based on the electrical loop.

Figure 14:
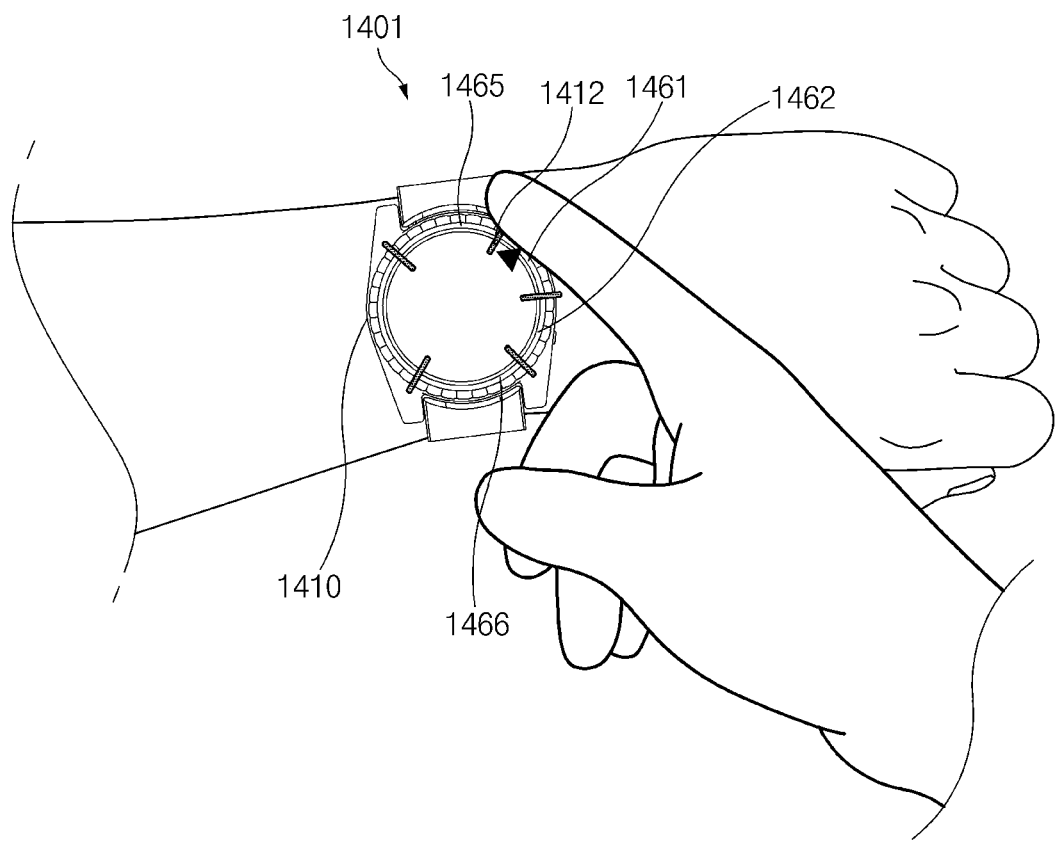
FIG. 14 is a diagram illustrating an example operation of an electronic device, according to various embodiments.

FIG. 14 is a diagram illustrating an example operation of an electronic device 1401, according to various embodiments.

FIG. 14 illustrates an operation of the electronic device 1401 when a touch input is applied to an electrode area exceeding the number required for the electronic device 1401 to identify ECG information. For example, a touch input to one electrode may be required for the electronic device 1401 to identify the ECG information.

According to an embodiment, the electronic device 1401 (e.g., the electronic device 601 of FIG. 6) may include a first electrode 1461 (e.g., the first electrode 661 of FIG. 6), a second electrode 1462 (e.g., the second electrode 662 of FIG. 6), a fifth electrode 1465 (e.g., the fifth electrode 665 of FIG. 6), a sixth electrode 1466 (e.g., the sixth electrode 666 in FIG. 6), and an antenna 1410 (e.g., the antenna 610 of FIG. 6) positioned on a front plate (e.g., the front plate 621 of FIG. 6) and a side surface (e.g., the side surface 110C of FIG. 1). For example, the first electrode 1461 may be spaced from the fifth electrode 1465 through a second segment 1412.

In an embodiment, when a touch input to an area including the first electrode 1461, the fifth electrode 1465, and the second segment 1412 is detected, the electronic device 1401 may select one electrode for obtaining an ECG signal from among the first electrode 1461 and the fifth electrode 1465 based on a specified criterion.

For example, the electronic device 1401 may obtain an ECG signal using the first electrode 1461 having low contact impedance among the first electrode 1461 and the second electrode 1462. While obtaining the ECG signal using the first electrode 1461, the electronic device 1401 may turn off the operation of the second electrode 1462.

For example, the electronic device 1401 may display various user interfaces on a display (e.g., the display 1020 of FIG. 10). For example, while obtaining the ECG signal using the first electrode 1461, the electronic device 1401 may display guide information (e.g., information indicating that the second electrode 1462 is turned off) associated with an operation state of the second electrode 1462 on a display. For example, while obtaining the ECG signal using the first electrode 1461, the electronic device 1401 may display a GUI (e.g., an arrow) indicating that a touch input to the first electrode 1461 is being continuously detected, in an area adjacent to the first electrode 1461 of the display. For another example, when the touch input to the first electrode 1461 is not normally detected while the electronic device 1401 obtains the ECG signal using the first electrode 1461, the electronic device 1401 may display guide information (not shown) for guiding the touch input to the first electrode 1461 on the display.

Figure 15:
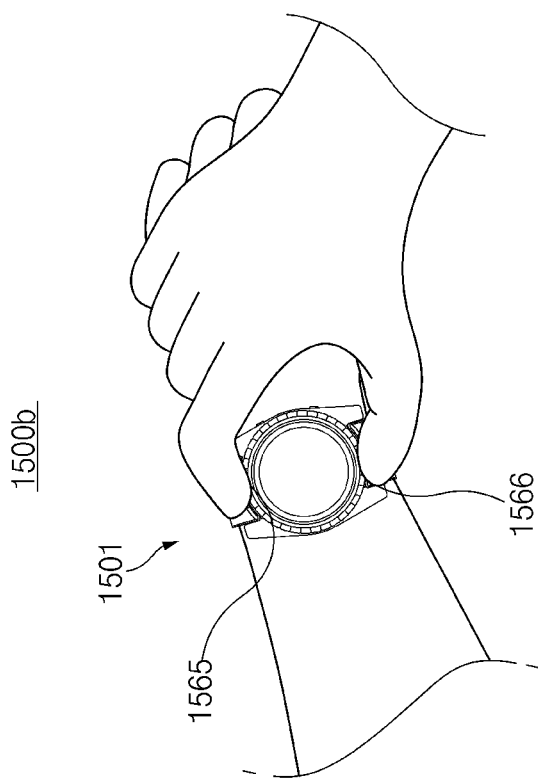
FIG. 15 is a diagram illustrating an example operation of an electronic device, according to various embodiments.
Figure 15:
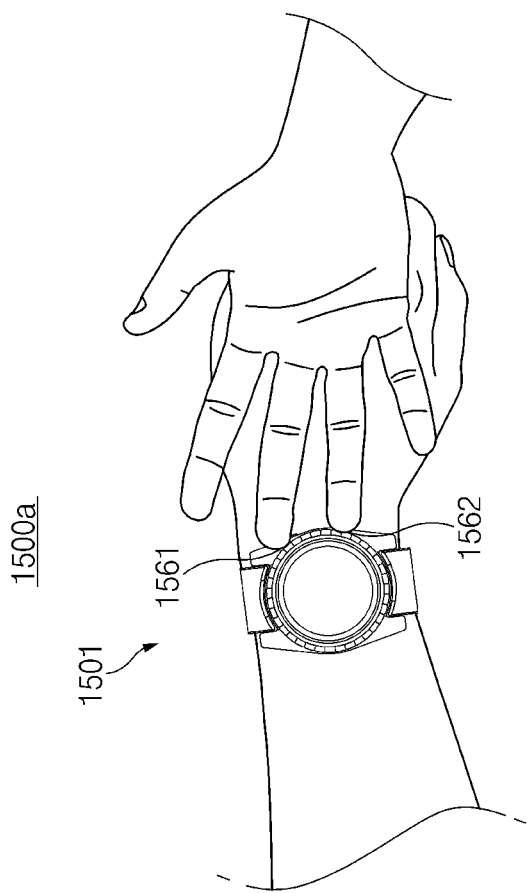

FIG. 15 is a diagram illustrating an example operation of an electronic device, according to various embodiments.

FIG. 15 may show an operation of an electronic device 1501 identifying a user's BIA information using two electrodes among a plurality of electrodes (e.g., the first electrode 661, the second electrode 662, the fifth electrode 665, and the sixth electrode 666 of FIG. 6) in a first electrode area positioned on a part of a front plate (e.g., the front plate 621 of FIG. 6) and a side surface (e.g., the side surface 110C of FIG. 1).

According to an embodiment, when a touch input to two of the plurality of electrodes included in the first electrode area is detected in a state where the electronic device 1501 is worn by the user, the electronic device 1501 may identify user biometric information through an electrode where the touch input is detected, while the touch input continues.

Referring to reference numeral 1500a, in an embodiment, while the touch input continues, when a touch input to a first electrode 1561 (e.g., the first electrode 661 of FIG. 6) and a second electrode 1562 (e.g., the second electrode 662 of FIG. 6) among a plurality of electrodes is detected, the electronic device 1501 may obtain a biometric signal through the first electrode 1561 and the second electrode 1562.

For example, the electronic device 1501 may identify an electrical loop formed through the first electrode 1561, the second electrode 1562, and a third electrode (e.g., the third electrode 663 of FIG. 7) and a fourth electrode (e.g., the fourth electrode 664 of FIG. 7) which are positioned within a second electrode area positioned on a rear plate (e.g., the rear plate 607 of FIG. 7), and may identify the user's BIA information based on the BIA signal obtained based on the electrical loop.

Referring to reference numeral 1500b, in an embodiment, when a touch input to a fifth electrode 1565 (e.g., the fifth electrode 665 of FIG. 6) and a sixth electrode 1566 (e.g., the sixth electrode 666 in FIG. 6) among a plurality of electrodes in a first electrode area is detected, the electronic device 1501 may obtain a biometric signal through the fifth electrode 1565 and the sixth electrode 1566.

For example, the electronic device 1501 may identify an electrical loop formed through the fifth electrode 1565, the sixth electrode 1566, the third electrode positioned on the rear plate, and the fourth electrode positioned on the rear plate, and may identify the user's BIA information based on the BIA signal obtained based on the electrical loop.

Figure 16:
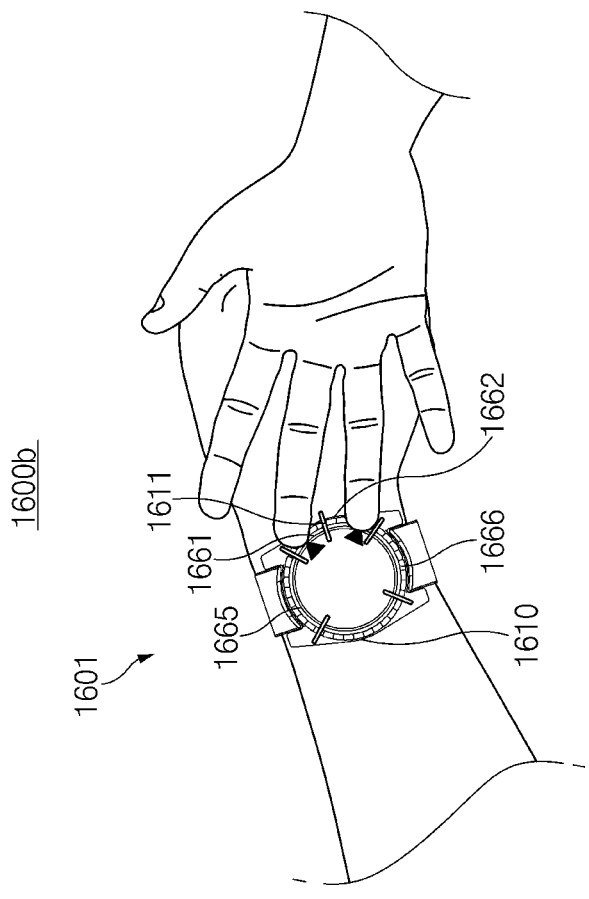
FIG. 16 is a diagram illustrating an example operation of an electronic device, according to various embodiments.
Figure 16:
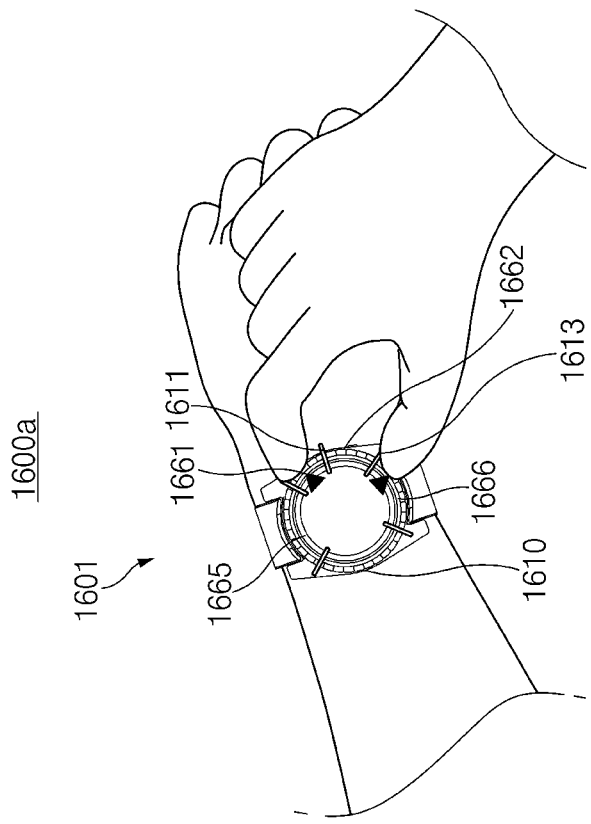

FIG. 16 is a diagram illustrating an example operation of an electronic device, according to various embodiments.

FIG. 16 illustrates an operation of an electronic device 1601 when a touch input is applied to an electrode area exceeding the number required for the electronic device 1601 to identify BIA information. For example, a user's touch input to two electrodes may be required for the electronic device 1601 to identify the BIA information.

According to an embodiment, the electronic device 1601 (e.g., the electronic device 601 of FIG. 6) may include a first electrode 1661 (e.g., the first electrode 661 of FIG. 6), a second electrode 1662 (e.g., the second electrode 662 of FIG. 6), a fifth electrode 1665 (e.g., the fifth electrode 665 of FIG. 6), a sixth electrode 1666 (e.g., the sixth electrode 666 in FIG. 6), and an antenna 1610 (e.g., the antenna 610 of FIG. 6) positioned on a front plate (e.g., the front plate 621 of FIG. 6) and a side surface (e.g., the side surface 110C of FIG. 1). For example, the first electrode 1661 may be arranged spaced from the second electrode 1662 through a first segment 1611 (e.g., the first segment 611 of FIG. 6). For example, the second electrode 1662 may be arranged spaced from the sixth electrode 1666 through a third segment 1613 (e.g., the third segment 613 of FIG. 6).

Referring to reference numeral 1600a, the electronic device 1601 may detect the user's touch input to an area including the first electrode 1661, the second electrode 1662, the first segment 1611, the third segment 1613, and the sixth electrode 1666. In this case, the electronic device 1601 may select one electrode for obtaining a BIA signal from among the second electrode 1662 and the sixth electrode 1666 based on a specified criterion.

For example, the electronic device 1601 may obtain the BIA signal using the second electrode 1662 having low contact impedance among the second electrode 1662 and the sixth electrode 1666. For example, while obtaining the BIA signal using the second electrode 1662, the electronic device 1601 may turn off the operation of the sixth electrode 1666. For example, while obtaining the BIA signal using the second electrode 1662, the electronic device 1601 may turn off operations of the remaining electrodes such as the fifth electrode 1665 and the sixth electrode 1666 other than the first electrode 1661 and the second electrode 1662 for obtaining the BIA signal from among a plurality of electrodes in the first electrode area.

Referring to reference numeral 1600b, the electronic device 1601 may detect the user's touch input to an area including the first electrode 1661, the second electrode 1662, and the first segment 1611. In this case, the electronic device 1601 may display a user interface including guide information for identifying BIA information on a display (e.g., the display 1020 of FIG. 10).

For example, while obtaining the BIA signal using the first electrode 1661 and the second electrode 1662, the electronic device 1601 may display a GUI (e.g., an arrow) indicating that a touch input to the first electrode 1661 and the second electrode 1662 is continuously being detected, in an area adjacent to the first electrode 1661 and the second electrode 1662 of the display.

For example, when the touch input to the first electrode 1661 or the second electrode 1662 is not normally detected while the electronic device 1401 obtains the BIA signal using the first electrode 1661 and the second electrode 1662, the electronic device 1401 may display guide information (not shown) for guiding a touch input to the first electrode 1661 or the second electrode 1662 on the display.

For example, the electronic device 1601 may display a GUI related to the touch input detected based on the touch input. For example, the electronic device 1601 may display a color of a GUI related to the touch input, an image included in the GUI, and/or a text included in the GUI based on at least one of the type of the touch input, the duration of the touch input, or the touch intensity of the touch input.

For example, when a touch input to the first segment 1611 continues, the electronic device 1601 may display guide information for inducing termination of the touch input to the first segment 1611 on the display.

For example, the electronic device 1601 may display guide information including the measurement progress of the BIA signal on the display. For example, the electronic device 1601 may display guide information indicating that the state of the touch input or the user's posture needs to be maintained while the electronic device 1601 displays the measurement progress.

Figure 17:
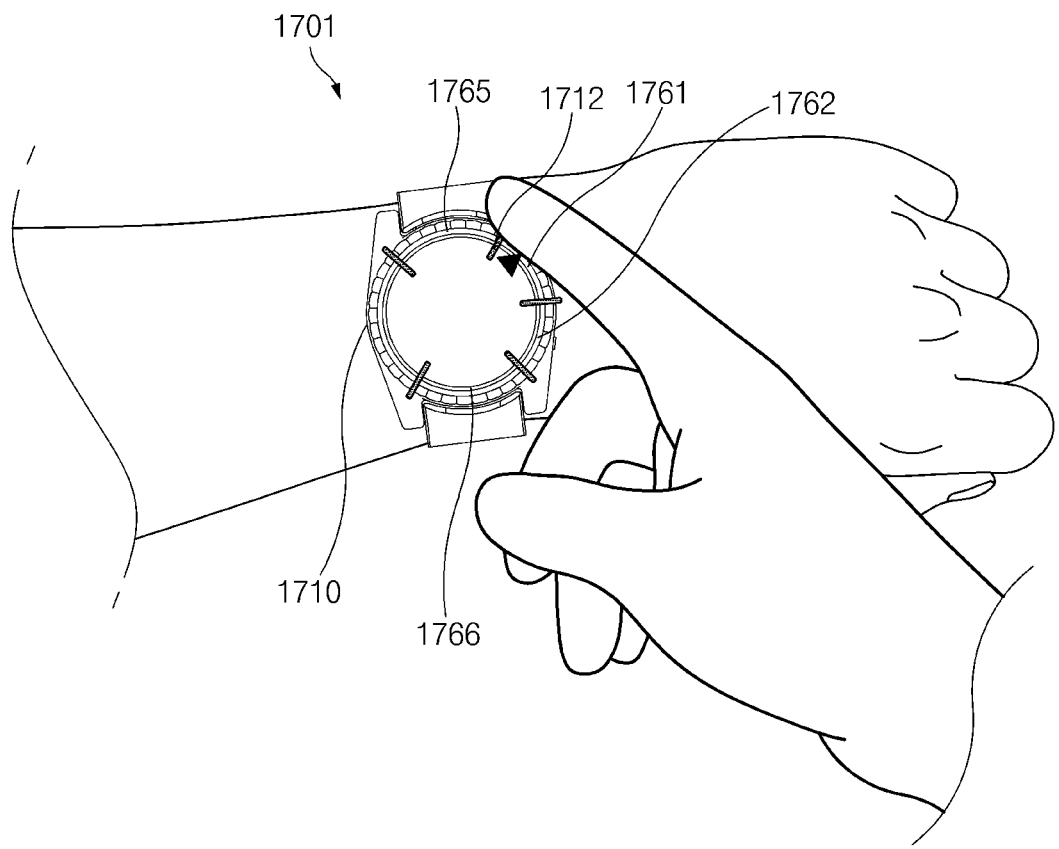
FIG. 17 is a diagram illustrating an example operation of an electronic device, according to various embodiments.

FIG. 17 is a diagram illustrating an example operation of an electronic device, according to various embodiments.

FIG. 17 illustrates an operation in which an electronic device 1701 provides BIA information when a user performs a touch input using one finger.

According to an embodiment, the electronic device 1701 (e.g., the electronic device 601 of FIG. 6) may include a first electrode 1761 (e.g., the first electrode 661 of FIG. 6), a second electrode 1762 (e.g., the second electrode 662 of FIG. 6), a fifth electrode 1765 (e.g., the fifth electrode 665 of FIG. 6), a sixth electrode 1766 (e.g., the sixth electrode 666 in FIG. 6), and an antenna 1710 (e.g., the antenna 610 of FIG. 6) positioned on a front plate (e.g., the front plate 621 of FIG. 6) and a side surface (e.g., the side surface 110C of FIG. 1). For example, the first electrode 1761 may be arranged spaced from the fifth electrode 1765 through a second segment 1712 (e.g., the second segment 612 of FIG. 6).

In an embodiment, the electronic device 1701 may detect a touch input to two electrodes, may obtain a BIA signal using electrodes to which the touch input is applied, while the touch input continues, and may identify the user's BIA information based on the obtained BIA signal.

In an embodiment, the electronic device 1701 may detect a touch input to an area including the first electrode 1761, the fifth electrode 1765, and the second segment 1712. In this case, the electronic device 1701 may identify an electrical loop formed through the first electrode 1761, the fifth electrode 1765, and a third electrode (e.g., the third electrode 663 of FIG. 7) and a fourth electrode (e.g., the fourth electrode 664 of FIG. 7) which are positioned within a second electrode area positioned on a rear plate (e.g., the rear plate 607 of FIG. 7), and may identify the user's BIA information based on the BIA signal obtained based on the electrical loop.

For example, while identifying the BIA information, the electronic device 1701 may display a user interface including information indicating that a touch input to the second segment 1712 continues, on a display (e.g., the display 1020 of FIG. 10). For example, when a touch input to the second segment 1712 continues, the electronic device 1701 may display guide information for inducing termination of the touch input to the second segment 1712 on the display.

FIG. 17 illustrates that a touch input to an area including two electrodes is applied. However, embodiments of the disclosure are not limited thereto. For example, while obtaining the BIA signal, the electronic device 1701 may identify that only the touch input to the first electrode 1761 is detected. In this case, the electronic device 1701 may display guide information related to an operation state of the second electrode 1762 on the display. For example, the electronic device 1701 may display, on the display, a user interface including information indicating that the second electrode 1762 is operating and/or information for guiding a touch input to the second electrode 1762 for identification of BIA information.

Figure 18:
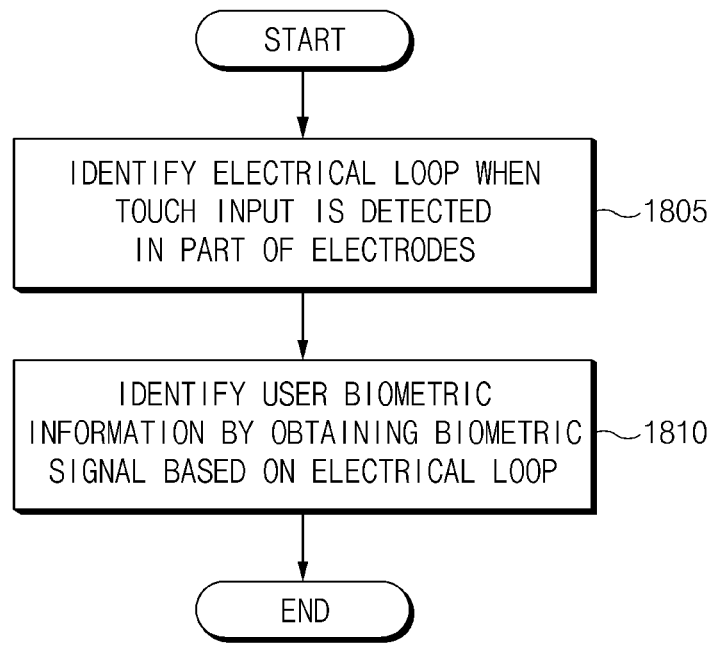
FIG. 18 is a flowchart illustrating an example operation of an electronic device, according to various embodiments.

FIG. 18 is a flowchart illustrating an example operation of an electronic device, according to various embodiments.

According to an embodiment, an electronic device (e.g., the electronic device 101 of FIG. 1 or the electronic device 601 of FIG. 6) may perform operations illustrated in FIG. 18. For example, a processor of the electronic device (e.g., the processor 620 of FIG. 6) may be configured to perform operations of FIG. 18 when instructions stored in a memory (e.g., the memory 950 of FIG. 9) are executed.

In operation 1805, when a touch input is detected in a part of the electrodes, the electronic device may identify an electrical loop. For example, when a touch input to at least part of a first electrode and a second electrode of a first electrode area positioned on a part of a front surface and a side surface of the electronic device is detected, the electronic device may identify an electrical loop, which is positioned on the first electrode, the second electrode, and a rear surface of the wearable electronic device and which is formed through the third electrode and the fourth electrode that are in contact with a part of the user's body, or a combination thereof.

In operation 1810, the electronic device may identify user biometric information by obtaining a biometric signal based on the electrical loop. For example, the electronic device may obtain ECG information or BIA information based on the biometric signal.

For example, when the first touch input to the first electrode in the first electrode area is detected, the electronic device may identify a first electrical loop formed through the first electrode, the third electrode, and the fourth electrode and may identify the user's ECG information based on the ECG signal formed based on the first electrical loop.

For example, when a second touch input to the area including the first electrode, the second electrode, and the first segment is detected, the electronic device may obtain an ECG signal using a first electrode having low contact impedance among the first electrode and the second electrode, and may identify the user's ECG information based on the obtained ECG signal. In this case, while obtaining the ECG signal using the first electrode, the electronic device may turn off the operation of the second electrode.

For example, when a third touch input to an area including the first electrode and the second electrode is detected, the electronic device may identify a second electrical loop formed through the first electrode, the second electrode, the third electrode, and the fourth electrode and may identify the user's BIA information based on the BIA signal obtained based on the second electrical loop.

For example, when a fourth touch input to an area including the sixth electrode, which is positioned in a part of the first electrode, the second electrode, a first segment, and a front surface and a side surface of the electronic device to be spaced from the second electrode through a third segment, is detected, the electronic device may obtain a BIA signal using the first electrode and the second electrode having low contact impedance from among the second electrode and the sixth electrode. In this case, while obtaining the BIA signal using the first electrode and the second electrode, the electronic device may turn off operations of the fifth electrode and the sixth electrode.

FIG. 19 is a block diagram illustrating an example electronic device 1901 in a network environment 1900 according to various embodiments. Referring to FIG. 19, the electronic device 1901 in the network environment 1900 may communicate with an electronic device 1902 via a first network 1998 (e.g., a short-range wireless communication network), or at least one of an electronic device 1904 or a server 1908 via a second network 1999 (e.g., a long-range wireless communication network). According to an embodiment, the electronic device 1901 may communicate with the electronic device 1904 via the server 1908. According to an embodiment, the electronic device 1901 may include a processor 1920, memory 1930, an input module 1950, a sound output module 1955, a display module 1960, an audio module 1970, a sensor module 1976, an interface 1977, a connecting terminal 1978, a haptic module 1979, a camera module 1980, a power management module 1988, a battery 1989, a communication module 1990, a subscriber identification module (SIM) 1996, or an antenna module 1997. In various embodiments, at least one of the components (e.g., the connecting terminal 1978) may be omitted from the electronic device 1901, or one or more other components may be added in the electronic device 1901. In various embodiments, some of the components (e.g., the sensor module 1976, the camera module 1980, or the antenna module 1997) may be implemented as a single component (e.g., the display module 1960).

The processor 1920 may execute, for example, software (e.g., a program 1940) to control at least one other component (e.g., a hardware or software component) of the electronic device 1901 coupled with the processor 1920, and may perform various data processing or computation. According to an embodiment, as at least part of the data processing or computation, the processor 1920 may store a command or data received from another component (e.g., the sensor module 1976 or the communication module 1990) in volatile memory 1932, process the command or the data stored in the volatile memory 1932, and store resulting data in non-volatile memory 1934. According to an embodiment, the processor 1920 may include a main processor 1921 (e.g., a central processing unit (CPU) or an application processor (AP)), or an auxiliary processor 1923 (e.g., a graphics processing unit (GPU), a neural processing unit (NPU), an image signal processor (ISP), a sensor hub processor, or a communication processor (CP)) that is operable independently from, or in conjunction with, the main processor 1921. For example, when the electronic device 1901 includes the main processor 1921 and the auxiliary processor 1923, the auxiliary processor 1923 may be adapted to consume less power than the main processor 1921, or to be specific to a specified function. The auxiliary processor 1923 may be implemented as separate from, or as part of the main processor 1921.

The auxiliary processor 1923 may control at least some of functions or states related to at least one component (e.g., the display module 1960, the sensor module 1976, or the communication module 1990) among the components of the electronic device 1901, instead of the main processor 1921 while the main processor 1921 is in an inactive (e.g., sleep) state, or together with the main processor 1921 while the main processor 1921 is in an active state (e.g., executing an application). According to an embodiment, the auxiliary processor 1923 (e.g., an image signal processor or a communication processor) may be implemented as part of another component (e.g., the camera module 1980 or the communication module 1990) functionally related to the auxiliary processor 1923. According to an embodiment, the auxiliary processor 1923 (e.g., the neural processing unit) may include a hardware structure specified for artificial intelligence model processing. An artificial intelligence model may be generated by machine learning. Such learning may be performed, e.g., by the electronic device 1901 where the artificial intelligence is performed or via a separate server (e.g., the server 1908). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 1930 may store various data used by at least one component (e.g., the processor 1920 or the sensor module 1976) of the electronic device 1901. The various data may include, for example, software (e.g., the program 1940) and input data or output data for a command related thereto. The memory 1930 may include the volatile memory 1932 or the non-volatile memory 1934.

The program 1940 may be stored in the memory 1930 as software, and may include, for example, an operating system (OS) 1942, middleware 1944, or an application 1946.

The input module 1950 may receive a command or data to be used by another component (e.g., the processor 1920) of the electronic device 1901, from the outside (e.g., a user) of the electronic device 1901. The input module 1950 may include, for example, a microphone, a mouse, a keyboard, a key (e.g., a button), or a digital pen (e.g., a stylus pen).

The sound output module 1955 may output sound signals to the outside of the electronic device 1901. The sound output module 1955 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 1960 may visually provide information to the outside (e.g., a user) of the electronic device 1901. The display module 1960 may include, for example, a display, a hologram device, or a projector and control circuitry to control a corresponding one of the display, hologram device, and projector. According to an embodiment, the display module 1960 may include a touch sensor adapted to detect a touch, or a pressure sensor adapted to measure the intensity of force incurred by the touch.

The audio module 1970 may convert a sound into an electrical signal and vice versa. According to an embodiment, the audio module 1970 may obtain the sound via the input module 1950, or output the sound via the sound output module 1955 or a headphone of an external electronic device (e.g., an electronic device 1902) directly (e.g., wiredly) or wirelessly coupled with the electronic device 1901.

The sensor module 1976 may detect an operational state (e.g., power or temperature) of the electronic device 1901 or an environmental state (e.g., a state of a user) external to the electronic device 1901, and then generate an electrical signal or data value corresponding to the detected state. According to an embodiment, the sensor module 1976 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1977 may support one or more specified protocols to be used for the electronic device 1901 to be coupled with the external electronic device (e.g., the electronic device 1902) directly (e.g., wiredly) or wirelessly. According to an embodiment, the interface 1977 may include, for example, a high definition multimedia interface (HDMI), a universal serial bus (USB) interface, a secure digital (SD) card interface, or an audio interface.

A connecting terminal 1978 may include a connector via which the electronic device 1901 may be physically connected with the external electronic device (e.g., the electronic device 1902). According to an embodiment, the connecting terminal 1978 may include, for example, a HDMI connector, a USB connector, a SD card connector, or an audio connector (e.g., a headphone connector).

The haptic module 1979 may convert an electrical signal into a mechanical stimulus (e.g., a vibration or a movement) or electrical stimulus which may be recognized by a user via his tactile sensation or kinesthetic sensation. According to an embodiment, the haptic module 1979 may include, for example, a motor, a piezoelectric element, or an electric stimulator.

The camera module 1980 may capture a still image or moving images. According to an embodiment, the camera module 1980 may include one or more lenses, image sensors, image signal processors, or flashes.

The power management module 1988 may manage power supplied to the electronic device 1901. According to an embodiment, the power management module 1988 may be implemented as at least part of, for example, a power management integrated circuit (PMIC).

The battery 1989 may supply power to at least one component of the electronic device 1901. According to an embodiment, the battery 1989 may include, for example, a primary cell which is not rechargeable, a secondary cell which is rechargeable, or a fuel cell.

The communication module 1990 may support establishing a direct (e.g., wired) communication channel or a wireless communication channel between the electronic device 1901 and the external electronic device (e.g., the electronic device 1902, the electronic device 1904, or the server 1908) and performing communication via the established communication channel. The communication module 1990 may include one or more communication processors that are operable independently from the processor 1920 (e.g., the application processor (AP)) and supports a direct (e.g., wired) communication or a wireless communication. According to an embodiment, the communication module 1990 may include a wireless communication module 1992 (e.g., a cellular communication module, a short-range wireless communication module, or a global navigation satellite system (GNSS) communication module) or a wired communication module 1994 (e.g., a local area network (LAN) communication module or a power line communication (PLC) module). A corresponding one of these communication modules may communicate with the external electronic device via the first network 1998 (e.g., a short-range communication network, such as Bluetooth™, wireless-fidelity (Wi-Fi) direct, or infrared data association (IrDA)) or the second network 1999 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1992 may identify and authenticate the electronic device 1901 in a communication network, such as the first network 1998 or the second network 1999, using subscriber information (e.g., international mobile subscriber identity (IMSI)) stored in the subscriber identification module 1996.

The wireless communication module 1992 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 1992 may support a high-frequency band (e.g., the mmWave band) to achieve, e.g., a high data transmission rate. The wireless communication module 1992 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 1992 may support various requirements specified in the electronic device 1901, an external electronic device (e.g., the electronic device 1904), or a network system (e.g., the second network 1999). According to an embodiment, the wireless communication module 1992 may support a peak data rate (e.g., 20 Gbps or more) for implementing eMBB, loss coverage (e.g., 1964 dB or less) for implementing mMTC, or U-plane latency (e.g., 0.5 ms or less for each of downlink (DL) and uplink (UL), or a round trip of 19 ms or less) for implementing URLLC.

The antenna module 1997 may transmit or receive a signal or power to or from the outside (e.g., the external electronic device) of the electronic device 1901. According to an embodiment, the antenna module 1997 may include an antenna including a radiating element including a conductive material or a conductive pattern formed in or on a substrate (e.g., a printed circuit board (PCB)). According to an embodiment, the antenna module 1997 may include a plurality of antennas (e.g., array antennas). In such a case, at least one antenna appropriate for a communication scheme used in the communication network, such as the first network 1998 or the second network 1999, may be selected, for example, by the communication module 1990 (e.g., the wireless communication module 1992) from the plurality of antennas. The signal or the power may then be transmitted or received between the communication module 1990 and the external electronic device via the selected at least one antenna. According to an embodiment, another component (e.g., a radio frequency integrated circuit (RFIC)) other than the radiating element may be additionally formed as part of the antenna module 1997.

According to various embodiments, the antenna module 1997 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 1901 and the external electronic device 1904 via the server 1908 coupled with the second network 1999. Each of the electronic devices 1902 or 1904 may be a device of a same type as, or a different type, from the electronic device 1901. According to an embodiment, all or some of operations to be executed at the electronic device 1901 may be executed at one or more of the external electronic devices 1902, 1904, or 1908. For example, if the electronic device 1901 should perform a function or a service automatically, or in response to a request from a user or another device, the electronic device 1901, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1901. The electronic device 1901 may provide the outcome, with or without further processing of the outcome, as at least part of a reply to the request. To that end, a cloud computing, distributed computing, mobile edge computing (MEC), or client-server computing technology may be used, for example. The electronic device 1901 may provide ultra low-latency services using, e.g., distributed computing or mobile edge computing. In an embodiment, the external electronic device 1904 may include an internet-of-things (IoT) device. The server 1908 may be an intelligent server using machine learning and/or a neural network. According to an embodiment, the external electronic device 1904 or the server 1908 may be included in the second network 1999. The electronic device 1901 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 1940) including one or more instructions that are stored in a storage medium (e.g., internal memory 1936 or external memory 1938) that is readable by a machine (e.g., the electronic device 1901). For example, a processor (e.g., the processor 1920) of the machine (e.g., the electronic device 1901) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to an example embodiment of the disclosure, a wearable electronic device may include: a housing including a first surface forming a front surface of the wearable electronic device, a second surface facing away from the first surface, and a side surface surrounding an internal space between the first surface and the second surface, a first electrode area positioned in a part of the first surface and the side surface and including a plurality of electrodes, an antenna positioned in a part of the first surface and the side surface and defined by the first electrode area and a segment area, a display visible through at least part of the first surface, a second electrode area positioned on the second surface, a processor, and a memory operatively connected to the processor and including instructions. For example, when executed by the processor, the instructions may cause the wearable electronic device to: obtain a biometric signal through the first electrode area, the second electrode area, or a combination of the first electrode area and the second electrode area based on a touch input to at least part of the first electrode area being detected, and perform wireless communication through the antenna.

According to an example embodiment, the wearable electronic device may further include: a first key button and a second key button positioned on the side surface and extending toward the internal space. For example, when executed by the processor, the instructions may cause the wearable electronic device to: obtain a biometric signal through the first electrode area, the second electrode area, the first key button, the second button, or a combination of the first electrode area, the second electrode area, the first key button, and the second button.

According to an example embodiment, the plurality of electrodes included in the first electrode area may include: a first electrode and a second electrode, spaced from each other through a first segment. The second electrode area may include a third electrode and a fourth electrode in contact with a part of a body. For example, when executed by the processor, the instructions may cause the wearable electronic device to: identify an electrical loop formed through the first electrode, the second electrode, the third electrode, the fourth electrode, or a combination of the first electrode, the second electrode, the third electrode, and the fourth electrode based on a touch input to at least part of the first electrode and the second electrode being detected, and identify biometric information based on the biometric signal obtained based on the electrical loop.

According to an example embodiment, when executed by the processor, the instructions may cause the wearable electronic device to: identify a first electrical loop formed through the first electrode, the third electrode, and the fourth electrode based on a first touch input to the first electrode being detected, and identify electrocardiogram (ECG) information based on an ECG signal obtained based on the first electrical loop.

According to an example embodiment, when executed by the processor, the instructions may cause the wearable electronic device to: obtain the ECG signal using the first electrode having low contact impedance among the first electrode and the second electrode based on a second touch input to an area including the first electrode, the second electrode, and the first segment being detected.

According to an example embodiment, when executed by the processor, the instructions may cause the wearable electronic device to: turn off an operation of the second electrode while obtaining the ECG signal using the first electrode.

According to an example embodiment, when executed by the processor, the instructions may cause the wearable electronic device to: identify a second electrical loop formed through the first electrode, the second electrode, the third electrode, and the fourth electrode based on a third touch input to an area including the first electrode and the second electrode being detected, and identify bioelectrical impedance analysis (BIA) information based on a BIA signal obtained based on the second electrical loop.

According to an example embodiment, when executed by the processor, the instructions may cause the wearable electronic device to: display guide information associated with an operation state of the second electrode on the display based on identifying that only a touch input to the first electrode is detected while the wearable electronic device obtains the BIA signal.

According to an example embodiment, the plurality of electrodes included in the first electrode area may further include a fifth electrode spaced from the first electrode through a second segment and a sixth electrode spaced from the second electrode through a third segment. When executed by the processor, the instructions may cause the wearable electronic device to: identify biometric information using the first electrode, the second electrode, the third electrode, the fourth electrode, the fifth electrode, the sixth electrode, or a combination of the first electrode, the second electrode, the third electrode, the fourth electrode, the fifth electrode, and the sixth electrode based on the touch input to at least part of the first electrode, the second electrode, the fifth electrode, and the sixth electrode being detected.

According to an example embodiment, when executed by the processor, the instructions may cause the wearable electronic device to: obtain the BIA signal using the first electrode and the second electrode having low contact impedance among the second electrode and the sixth electrode based on a fourth touch input to an area including the first electrode, the second electrode, the first segment, the third segment, and the sixth electrode being detected.

According to an example embodiment, when executed by the processor, the instructions may cause the wearable electronic device to: turn off operations of the fifth electrode and the sixth electrode while obtaining the BIA signal using the first electrode and the second electrode.

According to an example embodiment, when executed by the processor, the instructions may cause the wearable electronic device to: display a user interface associated with operation states of the plurality of electrodes on the display, and change an operation state of at least one of the first electrode, the second electrode, the fifth electrode, or the sixth electrode based on a specified input to the user interface being detected.

According to an example embodiment, the wearable electronic device may further include: a ground shield positioned between a BIA signal line configured to obtain a BIA signal and an ECG signal line configured to obtain an ECG signal.

According to an example embodiment, when executed by the processor, the instructions may cause the wearable electronic device to: provide a haptic function to an area where the touch input is detected based on the touch input to the at least part of the first electrode area being detected.

According to an example embodiment, each of the plurality of electrodes may include a coating layer comprising indium tin oxide (ITO), CrSiCN, or a combination of ITO and CrSiCN and a body layer comprising ceramic, gorilla glass, or a combination of ceramic and gorilla glass. For example, each of the plurality of electrodes may be electrically connected to a printed circuit board (PCB) positioned inside the housing through a connector in contact with a part of the coating layer.

According to an example embodiment of the disclosure, a method in which a wearable electronic device obtains a biometric signal may include: identifying an electrical loop positioned on a first electrode, a second electrode, and a rear surface of the wearable electronic device and formed through a third electrode and a fourth electrode in contact with a part of a body, or a combination of the third electrode and the fourth electrode based on a touch input to at least part of a first electrode and a second electrode positioned in a part of a front surface and a side surface of the wearable electronic device being detected, identifying biometric information based on a biometric signal obtained based on the electrical loop, and performing wireless communication through an antenna defined by the first electrode, the second electrode, and a segment area. For example, the first electrode and the second electrode may be spaced from each other through a first segment.

According to an example embodiment, the identifying of the electrical loop by the wearable electronic device may include: identifying a first electrical loop formed through the first electrode, the third electrode, and the fourth electrode based on a first touch input to the first electrode being detected, and identifying ECG information based on an ECG signal obtained based on the first electrical loop.

According to an example embodiment, the identifying of the ECG information may include: obtaining the ECG signal using the first electrode having a low contact impedance among the first electrode and the second electrode and identifying ECG information based on the obtained ECG signal based on a second touch input to an area including the first electrode, the second electrode, and the first segment being detected, and turning off an operation of the second electrode while obtaining the ECG signal using the first electrode.

According to an example embodiment, the identifying of the electrical loop by the wearable electronic device may include: identifying a second electrical loop formed through the first electrode, the second electrode, the third electrode, and the fourth electrode based on a third touch input to an area including the first electrode and the second electrode being detected, and identifying BIA information of the user based on a BIA signal obtained based on the second electrical loop.

According to an example embodiment, the identifying of the BIA information may include: obtaining the BIA signal using the first electrode and the second electrode having low contact impedance among the second electrode and the sixth electrode based on a fourth touch input to an area including a sixth electrode positioned in the first electrode, the second electrode, the first segment, and a part of the front surface and the side surface of the wearable electronic device spaced from the second electrode through a third segment, and the third segment, being detected, and turning off operations of the fifth electrode and the sixth electrode while obtaining the BIA signal using the first electrode and the second electrode.

According to various example embodiments of the disclosure, it is possible to provide a wearable device in which an antenna and an electrode are placed in a part of housing.

According to various example embodiments of the disclosure, the wearable electronic device may provide a free and convenient biometric information measurement function through electrode arrangement positioned in consideration of usability.

According to various example embodiments of the disclosure, the wearable electronic device improved in terms of aesthetics and functionality may be provided by efficiently utilizing the housing area of the limited area.

Besides, a variety of effects directly or indirectly understood through the disclosure may be provided.

While the disclosure has been illustrated and described with reference to various example embodiments thereof, it will be understood that the various example embodiments are intended to be illustrative, not limiting. It will be further understood by those skilled in the art that various changes in form and detail may be made without departing from the true spirit and full scope of the disclosure including the appended claims and their equivalents. It will also be understood that any of the embodiment(s) described herein may be used in conjunction with any other embodiment(s) described herein.

What is claimed is:

1. A wearable electronic device comprising:
a housing including a first surface forming a front surface of the wearable electronic device, a second surface facing away from the first surface, and a side surface surrounding an internal space between the first surface and the second surface;
a first group of electrodes positioned in a part of the first surface and the side surface and including at least three electrodes, wherein the at least three electrodes comprises a first electrode, a second electrode, and a third electrode;
an antenna positioned in a part of the first surface and the side surface and defined by the first group of electrodes;
a display visible through at least part of the first surface;
a second group of electrodes positioned on the second surface and including at least a fourth electrode and a fifth electrode;
a processor configured to obtain a biometric signal through an electrical loop set based on the second group of electrodes and some of the at least three electrodes,
wherein each of the first electrode, the second electrode and the third electrode is configured to obtain the biometric signal;
wherein each of the fourth electrode and the fifth electrode is configured to obtain the biometric signal; and
wherein the processor is configured to,
based on a first touch input to any one electrode among the at least three electrodes, being detected, set a first electrical loop using the one electrode which the first touch input is detected, the fourth electrode, and the fifth electrode; and
based on a second touch input to any two electrodes among the at least three electrodes, being detected, set a second electrical loop using the two electrodes which the second touch input is detected, the fourth electrode, and the fifth electrode.

2. The wearable electronic device of claim 1, further comprising:
a key button positioned on the side surface and extending toward the internal space,
wherein the processor is configured to:
based on a third touch input to the key button being detected, set the first electrical loop based on the key button which the third touch input is detected, the fourth electrode, and the fifth electrode
based on a fourth touch input to the one electrode among the at least three electrodes and the key button, being detected, set the second electrical loop based on the fourth electrode, the fifth electrode, and the key button and the one electrode which the fourth touch input is detected.

3. The wearable electronic device of claim 1, wherein the processor is configured to:
identify biometric information based on the biometric signal obtained through the electrical loop.

4. The wearable electronic device of claim 3, wherein the biometric information identified based on the biometric signal obtained through the first electrical loop comprises electrocardiogram (ECG) information.

5. The wearable electronic device of claim 1, wherein the processor is configured to:
while obtaining the biometric signal through the first electrical loop, turn off an operation of the other two electrodes which the first touch input is not detected among the at least three electrodes.

6. The wearable electronic device of claim 1, wherein the processor is configured to:
based on identifying that only a touch input to the one electrode is detected while obtaining the biometric signal through the second electrical loop, display guide information associated with an operation state of the other electrode which the second touch input is not detected among the two electrodes on the display.

7. The wearable electronic device of claim 1, wherein the processor is configured to:
while obtaining the biometric signal through the second electrical loop, turn off an operation of the other electrode which the second touch input is not detected among the at least three electrodes.

8. The wearable electronic device of claim 3, wherein the biometric information identified based on the biometric signal obtained through the second electrical loop comprises bioelectrical impedance analysis (BIA) information.

9. The wearable electronic device of claim 1, wherein the processor is configured to:
display a user interface associated with operation states of the first group of electrodes on the display; and based on a specified input to the user interface being detected, change an operation state of at least one of the first electrode, the second electrode or the third electrode.

10. The wearable electronic device of claim 1, further comprising:
a ground shield positioned between a first signal line configured to obtain a first biometric signal obtained through the first electrical loop and an second signal line configured to obtain second biometric signal obtained through the second electrical loop.

11. The wearable electronic device of claim 1, wherein the processor is configured to:
based on the touch input to the at least part of the first group of electrodes being detected, provide a haptic function to an area where the touch input is detected.

12. The wearable electronic device of claim 1, wherein each of the first group of electrodes includes:
a coating layer comprising indium tin oxide (ITO), CrSiCN, or a combination of ITO and CrSiCN; and
a body layer comprising ceramic, gorilla glass, or a combination of ceramic and gorilla glass,
wherein each of the first group of electrodes is electrically connected to a printed circuit board (PCB) positioned inside the housing through a connector in contact with a part of the coating layer.

13. A method in which a wearable electronic device obtains a biometric signal, the method comprising:
determining some of electrode which a touch input is detected from among a first group of electrodes including at least three electrodes positioned in a part of a front surface and a side surface of the wearable electronic device; and
obtaining the biometric signal through an electrical loop set based on the some of the at least three electrodes and a second group of electrodes positioned on a rear surface of the wearable electronic device,
wherein the at least three electrodes includes at least a first electrode, a second electrode, and a third electrode, and the second group of electrodes includes at least a fourth electrode and a fifth electrode,
wherein each of the first electrode, the second electrode and the third electrode is configured to obtain the biometric signal, and
wherein each of the fourth electrode and the fifth electrode is configured to obtain the biometric signal,
further comprising:
based on a first touch input to any one electrode among the at least three electrodes, being detected, setting a first electrical loop using the one electrode which the first touch input is detected, the fourth electrode, and the fifth electrode; and
based on a second touch input to any two electrodes among the at least three electrodes, being detected, setting a second electrical loop using the two electrodes which the second touch input is detected, the fourth electrode, and the fifth electrode.

14. The method of claim 13, further comprising:
identifying electrocardiogram (ECG) information based on the biometric signal obtained through the first electrical loop, and
identifying impedance analysis (BIA) information based on the biometric signal obtained through the second electrical loop.

15. The method of claim 13, wherein the obtaining the biometric signal through the first electrical loop includes:
controlling the wearable electronic device to turn off an operation of the other two electrodes which the first touch input is not detected among the at least three electrodes.

16. The method of claim 13, wherein the obtaining the biometric signal through the second electrical loop includes:
controlling the wearable electronic device to turn off an operation of the other electrode which the second touch input is not detected among the at least three electrodes.

17. The method of claim 13, further comprising:
displaying a user interface associated with operation states of the first group of electrodes on the display; and
based on a specified input to the user interface being detected, changing an operation state of at least one of the first electrode, the second electrode, or the third electrode.

* * * * *